(12) United States Patent
Amano et al.

(10) Patent No.: US 8,232,300 B2
(45) Date of Patent: Jul. 31, 2012

(54) TRICYCLIC AMIDE COMPOUND

(75) Inventors: Yohei Amano, Tokyo (JP); Masayuki Noguchi, Chiba (JP); Koichi Shudo, Tokyo (JP)

(73) Assignee: Research Foundation Itsuu Laboratory, Tokyo (JP)

( * ) Notice: Subject to any disclaimer, the term of this patent is extended or adjusted under 35 U.S.C. 154(b) by 16 days.

(21) Appl. No.: 12/673,207

(22) PCT Filed: Aug. 14, 2008

(86) PCT No.: PCT/JP2008/064576
§ 371 (c)(1),
(2), (4) Date: Feb. 12, 2010

(87) PCT Pub. No.: WO2009/022721
PCT Pub. Date: Feb. 19, 2009

(65) Prior Publication Data
US 2011/0213157 A1    Sep. 1, 2011

(30) Foreign Application Priority Data

Aug. 15, 2007    (JP) .................................. 2007-211650

(51) Int. Cl.
| C07D 333/36 | (2006.01) |
| C07D 211/68 | (2006.01) |
| C07D 211/80 | (2006.01) |
| C07C 63/00  | (2006.01) |
| C07C 65/00  | (2006.01) |
| A61K 31/38  | (2006.01) |
| A61K 31/045 | (2006.01) |

(52) U.S. Cl. .......... 514/354; 549/77; 562/405; 514/448; 514/727; 546/285

(58) Field of Classification Search ........................ None
See application file for complete search history.

(56) References Cited

U.S. PATENT DOCUMENTS

| 5,162,588 | A |   | 11/1992 | Fehr et al. |
| 5,185,318 | A |   | 2/1993  | Fehr et al. |
| 5,324,875 | A |   | 6/1994  | Fehr et al. |
| 5,420,145 | A | * | 5/1995  | Shudo ............................ 514/352 |
| 5,442,124 | A |   | 8/1995  | Fehr et al. |
| 5,559,272 | A |   | 9/1996  | Fehr et al. |
| 6,420,363 | B1 | * | 7/2002 | Hibi et al. .................. 514/230.5 |

FOREIGN PATENT DOCUMENTS

| JP | 61-022047 | 1/1986 |
| JP | 61-076440 | 4/1986 |
| JP | 3-044348  | 2/1991 |
| JP | 9-071566  | 3/1997 |

OTHER PUBLICATIONS

Hibi, S. et al. Syntheses and Structure-Activity Relationships of Novel Retinoid X Receptor Agonists. J. Med. Chem. 1998, vol. 41, p. 3246, Chart 2.*
U.S. Appl. No. 12/673,177 to Hideaki Muratake et al., which application is the National Stage of PCT/JP2008/064575, filed Aug. 14, 2008.
U.S. Appl. No. 12/673,221 to Yohei Amano et al., which application is the National Stage of PCT/JP2008/064577, filed Aug. 14, 2008.
Edward Piers et al., "Synthesis of functionalized hexahydro-, octahydro-, and decahydro-1H-phenalenes via Diels-Alder reactions of 1-methylene-4a-methoxycarbonyl-1,2,3,4,4a,5,6,7-octahydronaphthalene and related dienes," Canadian Journal of Chemistry, vol. 71, No. 9, pp. 1463-1483, compound 58, 1993.
Lars Eklund et al., "Synthetic studies towards pseudopterosin A," Journal of the Chemical Society, Perkin Transactions 1: Organic and Bio-Organic Chemistry, No. 4, pp. 303-305, compound 8, 1996.
James P. Davidson et al., "First enantiospecific total synthesis of the antitubercular marine natural product pseudopteroxazole. Revision of assigned stereochemistry," Journal of the American Chemical Society, vol. 125, No. 44, pp. 13486-13489, compound 23, 2003.
International Search Report that issued with respect to PCT/JP2008/064576, mailed Sep. 16, 2008.
International Preliminary Report on Patentability, including the Written Opinion (in English) that issued with respect to PCT/JP2008/064576, mailed Feb. 25, 2010.
S. Karrman et al., Database Beilstein [Online] Beilstein Institute for Organic Chemistry, Frankfurt-Main, DE, Database accession No. 3475811 (BRN), 1945.
Extended European Search Report that issued with respect to European Patent Application No. 08792457.7, mailed Jul. 6, 2010.

* cited by examiner

*Primary Examiner* — Rita Desai
*Assistant Examiner* — Ben S Michelson
(74) *Attorney, Agent, or Firm* — Greenblum & Bernstein, P.L.C.

(57) ABSTRACT

A compound represented by the following general formula (I):

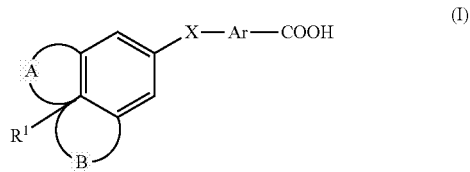

[wherein $R^1$ represents hydrogen atom or a $C_{1-6}$ alkyl group, A and B represent —$(CH_2)_2$—, —$(CH_2)_3$—or —$(CH_2)_4$—, X represents —$N(R^2)$—CO—($R^2$ represents hydrogen atom or a $C_{1-6}$ alkyl group), —CO—$N(R^3)$—($R^3$ represents hydrogen atom or a $C_{1-6}$ alkyl group), —$C(R^4)$=$C(R^5)$—($R^4$ and $R^5$ represent hydrogen atom or a $C_{1-6}$ alkyl group), or —$N(R^6)$—$SO_2$—($R^6$ represents hydrogen atom or a $C_{1-6}$ alkyl group), and Ar represents an aryldiyl group or a heteroaryldiyl group], which has a retinoid action and is useful as an active ingredient of a medicament.

5 Claims, No Drawings

TRICYCLIC AMIDE COMPOUND

TECHNICAL FIELD

The present invention relates to a tricyclic amide compound having a retinoid action.

BACKGROUND ART

Retinoic acid (vitamin A acid), an active metabolite of vitamin A, has extremely important physiological functions, e.g., inducing differentiation of immature cells under development processes toward mature cells having specific functions, enhancement of cell proliferation, life support action, and the like. Retinoic acid and compounds having retinoic acid-like biological activities are collectively referred to as "retinoids".

It has been proved that all-trans retinoic acid, considered as a biological retinoid, regulates proliferation and differentiation of animal cells, cellular mortalities, and the like. It has also been revealed that various vitamin A derivatives synthesized so far also have similar physiological functions, for example, the benzoic acid derivatives disclosed in Japanese Patent Unexamined Publication (KOKAI) Nos. 61-22047 and 61-76440, the compounds described in Journal of Medicinal Chemistry, 31 (11), 2182, 1988, and the like. Furthermore, various synthetic retinoids are exemplified in Adv. Drug Res., 24, 81, 1993 and J. Med. Chem., 48, 5875, 2005. For example, it is suggested that 4-[(5,6,7,8-tetrahydro-5,5,8,8-tetramethyl-2-naphthalenyl)carbamoyl]benzoic acid (Am80) also exhibits physiological actions similar to (but different from) those of retinoic acid (Cell Structure Funct., 16, 113, 1991; Biochem. Biophys. Res. Com., 166, 1300, 1990). Besides these, it has been demonstrated that various compounds have retinoic acid-like activity, such as the heterocyclic ring-containing carboxylic acid derivatives (Japanese Patent Unexamined Publication No. 9-71566).

For retinoids, various pre-clinical and clinical researches have been conducted for use of them as a medicament for therapeutic or prophylactic treatment of skin diseases, autoimmune diseases, lipid or sugar metabolic disorders, cranial nerve diseases, and malignant tumors. For example, it has been found that they are useful for therapeutic or prophylactic treatment of hyperkaratosis of epithelial tissue, rheumatism, delayed allergy, multiple sclerosis, autoimmune diseases, bone diseases, leukemia, certain types of cancers and cranial nerve diseases, spinal cord injury, cardiovascular diseases such as arteriosclerosis, vasoconstriction or restenosis, and control of neovascularization, diabetes, and disorder of lipid metabolism. As described above, retinoids are characterized by having various biological activities and pharmacological activities, and thus being applicable to various diseases as objects of therapeutic treatment. However, it cannot necessarily be considered that they are practically used as satisfactory medicaments in view of selectivity for the action and action site, kinetics in the living bodies such as that for absorption and excretion, and side reactions, because of such diversity as described above.

Therefore, retinoids exhibiting limited actions, or those showing metabolism, absorption, excretion, and distribution suitable for a specific object of therapeutic treatment are desired. For example, for internal diseases, a retinoid showing less action on the skin is preferred, and for the skin, a retinoid having characteristics suitable for external preparations is desired. Further, for chronic diseases, a retinoid compound showing prolonged action is preferred, for various kinds of cancers, a retinoid which acts on dividing cells such as cancer cells at an optimum concentration different from that for non-dividing cells is preferred, and for cranial nerve diseases, a retinoid showing high permeability for the blood-brain barrier, and superior distribution in cranial nerves is desired. Moreover, a retinoid showing less side reactions is desirable as a medicament.

DISCLOSURE OF THE INVENTION

Object to be Achieved by the Invention

An object of the present invention is to provide a novel compound having a retinoid action and useful as an active ingredient of a medicament.

Means for Achieving the Object

The inventors of the present invention conducted various researches in order to achieve the aforementioned object, and as a result, found that the compounds represented by the following general formula had a desired retinoid action. The present invention was accomplished on the basis of the aforementioned finding.

The present invention thus provides a compound represented by the following general formula (I):

[Formula 1]

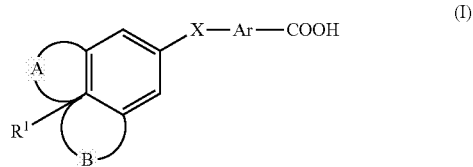

[wherein $R^1$ represents hydrogen atom or a $C_{1-6}$ alkyl group, A and B independently represent —$(CH_2)_2$—, —$(CH_2)_3$— or —$(CH_2)_4$—, X represents —N($R^2$)—CO— ($R^2$ represents hydrogen atom or a $C_{1-6}$ alkyl group), —CO—N($R^3$)— ($R^3$ represents hydrogen atom or a $C_{1-6}$ alkyl group), —C($R^4$)=C($R^5$)— ($R^4$ and $R^5$ independently represent hydrogen atom or a $C_{1-6}$ alkyl group), or —N($R^6$)—$SO_2$— ($R^6$ represents hydrogen atom or a $C_{1-6}$ alkyl group), and Ar represents an aryldiyl group or a heteroaryldiyl group], a salt thereof, or an ester thereof.

According to a preferred embodiment of the aforementioned invention, there is provided the aforementioned compound represented by the general formula (I), a salt thereof, or an ester thereof, wherein $R^1$ is hydrogen atom or methyl group, A and B both represent —$(CH_2)_3$— or —$(CH_2)_4$—, X is —NH—CO— or —CO—NH—, and Ar is a phenylene group, a pyridinediyl group, or a thiophenediyl group.

As a preparation intermediate of the aforementioned compound represented by the general formula (I), a compound represented by the aforementioned general formula (I), wherein X—Ar—COOH is X' (X' represents —COOH or —$NH_2$), or a salt thereof is also provided.

From another aspect of the present invention, there is provided a medicament comprising a compound represented by the aforementioned general formula (I), a physiologically acceptable salt thereof, or an ester thereof. This medicament can be used as an agent having a retinoid action.

The present invention further provides use of a compound represented by the aforementioned general formula (I), a physiologically acceptable salt thereof, or an ester thereof for manufacture of the aforementioned medicament, and a method for prophylactic and/or therapeutic treatment of a disease preventable and/or curable by administration of a retinoid, which comprises the step of administering an effective amount of a compound represented by the aforementioned general formula (I), a physiologically acceptable salt thereof, or an ester thereof to a mammal including human.

BEST MODE FOR CARRYING OUT THE INVENTION

In the specification, the alkyl group may be any of a linear alkyl group, a branched alkyl group, a cyclic alkyl group, and an alkyl group consisting of a combination these. The same shall apply to an alkyl moiety of other substituents having the alkyl moiety (alkoxyl group and the like).

As the $C_{1-6}$ alkyl group represented by $R^1$, a linear or branched alkyl group is preferred, a linear or branched $C_{1-4}$ alkyl group is more preferred, and methyl group is still more preferred. It is particularly preferred that $R^1$ is hydrogen atom or methyl group, and it is most preferred that $R^1$ is hydrogen atom. The $C_{1-6}$ alkyl group represented by $R^1$ may have a substituent. Type, substituting position, and number of the substituent are not particularly limited. Examples of the substituent include, for example, a halogen atom (fluorine atom, chlorine atom, bromine atom, or iodine atom), hydroxyl group, an alkoxy group, amino group, oxo group, and the like, but the substituent is not limited to these examples.

A and B independently represent —$(CH_2)_2$—, —$(CH_2)_3$— or —$(CH_2)_4$—. It is preferred that both A and B represent —$(CH_2)_3$—, or both represent —$(CH_2)_4$—. When both A and B represent —$(CH_2)_3$—, it is preferred that $R^1$ is hydrogen atom or methyl group, and when both A and B represent —$(CH_2)_4$—, it is preferred that IV is hydrogen atom. The trimethylene group or tetramethylene group represented by A or B may have a substituent. Type, substituting position, and number of the substituent are not particularly limited. Examples of the substituent include, for example, a $C_{1-4}$ alkyl group, a $C_{1-4}$ alkoxyl group, a halogen atom (fluorine atom, chlorine atom, bromine atom, or iodine atom), hydroxyl group, an alkoxyl group, amino group, oxo group, and the like, but the substituent is not limited to these examples.

In —$N(R^2)$—CO—, —CO—$N(R^3)$—, —$C(R^4)$=C $(R^5)$—, or —$N(R^6)$—$SO_2$— represented by X, $R^2$, $R^3$, $R^4$, $R^5$ and $R^6$ preferably represent hydrogen atom or a $C_{1-4}$ alkyl group, and it is more preferred that $R^2$, $R^3$, $R^4$, $R^5$, and $R^6$ represent hydrogen atom. As X, —NH—CO— or —CO—NH— is preferred.

The aryl ring constituting the aryldiyl group represented by Ar may be a monocyclic aryl ring or a condensed aryl ring, and a 6- to 14-membered aryl ring can be used. More specifically, examples include, for example, benzene ring, naphthalene ring, and the like. As the aryl ring, benzene ring is preferred. The binding positions of the aryldiyl group are not particularly limited, and it may binds at positions at which it can bind. For example, in the case of phenylene group, said group may be any of 1,2-phenylene group, 1,3-phenylene group, and 1,4-phenylene group.

Although type and number of heteroatoms contained in the heteroaryl ring constituting the heteroaryldiyl group represented by Ar are not particularly limited, a heteroaryl ring containing one or more heteroatoms selected from the group consisting of nitrogen atom, oxygen atom and sulfur atom as ring-constituting atoms is preferred. When two or more heteroatoms are contained, they may be the same or different. The heteroaryl ring may be a monocyclic heteroaryl ring or a condensed heteroaryl ring. More specifically, examples include, for example, pyridine ring, pyrimidine ring, pyrazine ring, pyridazine ring, triazine ring, quinoline ring, isoquinoline ring, quinazoline ring, phthalazine ring, quinoxaline ring, naphthylidine ring, cinnoline ring, thiophene ring, furan ring, pyrrole ring, imidazole ring, pyrazole ring, triazole ring, tetrazole ring, oxazole ring, thiazole ring, benzothiazole ring, benzofuran ring, indole ring, indazole ring, benzimidazole ring, benzotriazole ring, benzoxazole ring, purine ring, and the like, but the heteroaryl ring is not limited to these examples. Among them, pyridine ring is preferred. The binding positions of the heteroaryldiyl group are not particularly limited, and said group can bind at arbitrary positions at which it can bind. For example, in the case of pyridinediyl group, said group may be any of 2,3-pyridinediyl group, 2,4-pyridinediyl group, 2,5-pyridinediyl group, and 2,6-pyridinediyl group. In the case of thiophenediyl group, said group may be any of 2,3-thiophenediyl group, 2,4-thiophenediyl group, 2,5-thiophenediyl group, and 3,4-thiophenediyl group.

The aryldiyl group and heteroaryldiyl group represented by Ar may have a substituent on the ring. Type, substituting position, and number of the substituent are not particularly limited. Examples of the substituent include, for example, a $C_{1-4}$ alkyl group, a $C_{1-4}$ alkoxyl group, a halogen atom (fluorine atom, chlorine atom, bromine atom, or iodine atom), hydroxyl group, an alkoxyl group, amino group, oxo group, and the like, but the substituent is not limited to these examples. For example, on the phenylene group, a halogen atoms (fluorine atom, chlorine atom and the like), hydroxyl group, an alkoxyl group (methoxy group), and the like may exist, and in this case, a monofluorophenylene group, a difluorophenylene group, a monochlorophenylene group, a dichlorophenylene group, a monohydroxyphenylene group, a monoalkoxyphenylene group, and the like are more preferred.

The compounds of the present invention represented by the general formula (I) may exist in the forms of acid addition salts or base addition salts, and any of such salts also fall within the scope of the present invention. Examples of the acid addition salts include mineral acid salts such as hydrochloride or hydrobromide, and organic acid salts such as p-toluenesulfonate, methanesulfonate, oxalate, or tartrate. As the base addition salts, metal salts such as, for example, sodium salt, potassium salt, magnesium salt, or calcium salt, ammonium salts, or organic amine salts such as triethylamine salt or ethanolamine salt, and the like may be used. Further, the compounds may exist in the forms of amino acid salts such as glycine salt.

As the ester of the compound of the present invention represented by general formula (I), a physiologically acceptable ester is preferred. Specific examples of preferred residues forming the ester include, for example, methyl group, ethyl group, propyl group, isopropyl group, butyl group, isobutyl group, t-butyl group, benzyl group, acetoxymethyl group, 1-(acetoxy)ethyl group, propionyloxymethyl group, 1-(propionyloxy)ethyl group, butyryloxymethyl group, 1-(butyryloxy)ethyl group, isobutylyloxymethyl group, 1-(isobutyryloxy)ethyl group, valeryloxymethyl group, 1-(valeryloxy)ethyl group, isovaleryloxymethyl group, 1-(isovaleryloxy)ethyl group, pivaloyloxymethyl group, 1-(pivaloyloxy)ethyl group, methoxycarbonyloxymethyl group, 1-(methoxycarbonyloxy)ethyl group, ethoxycarbonyloxymethyl group, 1-(ethoxycarbonyloxy)ethyl group, propoxycarbonyloxymethyl group, 1-(propoxycarbonyloxy)ethyl group, isopropoxycarbonyloxymethyl group, 1-(isopropoxycarbonyloxy)ethyl group, butoxycarbonyloxymethyl group, 1-(buthoxycarbonyloxy)ethyl group, isobutoxycarbonyloxymethyl group, 1-(isobuthoxycarbonyloxy)ethyl group, t-buthoxycarbonyloxymethyl group, 1-(t-buthoxycarbonyloxy)ethyl group, cyclopentanecarbonyloxymethyl group, 1-(cyclopentanecarbonyloxy)ethyl group, cyclohexanecarbonyloxymethyl group, 1-(cyclohexanecarbonyloxy)ethyl group, cyclopenthyloxycarbonyloxymethyl group, 1-(cyclopenthyloxycarbonyloxy)ethyl group, cyclohexyloxycarbonyloxymethyl group, 1-(cyclohexyloxycarbonyloxy)ethyl group, benzoyloxymethyl group, 1-(benzoyloxy)ethyl group, phenoxycarbonyloxymethyl group, 1-(phenoxycarbonyloxy)ethyl group, (5-methyl-2-oxo-1,3-dioxoren-4-yl)methyl group, 2-trimethylsilylethyl group, and the like, but the examples are not limited to these examples.

The compounds of the present invention may have one or more asymmetric carbon atoms depending on types of substituents. Arbitrary optical isomers based on these asymmetric carbon atoms, arbitrary mixtures of optical isomers, racemates, diastereomers based on two or more asymmetric carbon atoms, arbitrary mixtures of diastereomers, and the like all fall within the scope of the present invention. Further, arbitrary hydrates or solvates of the compounds in free form or in the form of a salt also fall within the scope of the present invention.

The preparation methods of preferred compounds among the compounds of the aforementioned formula (I) are specifically described in the examples given in the present specification. Therefore, any compounds falling within the scope of the present invention can be prepared by suitably selecting starting materials, reaction regents, reaction conditions and the like used in those preparation methods, and if necessary, appropriately modifying or altering the preparation methods. However, the preparation methods of the compounds of the present invention are not limited to those specifically explained in the examples.

The compounds represented by the aforementioned general formula (I) and salts thereof have retinoid-like physiological activities (typical examples include cell differentiating activity, cell proliferation enhancing activity, life supporting activity and the like). Although it is not intended to be bound by any specific theory, the compounds and salts thereof of the present invention are characterized by having an extremely potent activation action on the retinoic acid receptor (RAR). Therefore, a medicament comprising a compound represented by general formula (I) or a physiologically acceptable salt thereof as an active ingredient is useful as an agent having a retinoid action. The medicament of the present invention containing the aforementioned active ingredient has, for example, cell differentiating activity, cell proliferation enhancing activity, life supporting activity and the like, and it can be used for prophylactic and/or therapeutic treatment of vitamin A deficiency disease, hyperkeratosis of epithelial tissue, psoriasis, allergic diseases, immunological diseases such as rheumatism, bone diseases, diabetes mellitus, leukemia, or cancers. Moreover, an ester of a compound represented by general formula (I) can be used as a prodrug of the compound represented by general formula (I), and it can also be similarly used as an active ingredient of a medicament.

The medicament of the present invention comprises, as an active ingredient, one or more kinds of substances selected from the group consisting of the compounds represented by the aforementioned general formula (I), physiologically acceptable salts thereof, and esters thereof. As the medicament of the present invention, the aforementioned substance, per se, may be administered. However, a pharmaceutical composition for oral administration or parenteral administration may preferably be administered which can be prepared by a method well known to those skilled in the art. Examples of the pharmaceutical compositions suitable for oral administrations include, for example, tablets, capsules, powders, subtilized granules, granules, liquids, syrups and the like. Examples of the pharmaceutical compositions suitable for parenteral administrations include, for example, injections, drops, suppositories, inhalants, eye drops, nasal drops, ointments, creams, patches, transdermal preparations, transmucosal preparations, and the like.

Examples of pharmaceutically acceptable additives used for preparation of the aforementioned pharmaceutical compositions include, for example, excipients, disintegrators and disintegrating aids, binders, lubricants, coating agents, colorants, diluents, base materials, dissolving agents and dissolving aids, isotonic agents, pH modifiers, stabilizers, propellants, adhesives and the like. They can be suitably selected by those skilled in the art depending on the form of the pharmaceutical composition, and two or more kinds of them may be used in combination. The aforementioned pharmaceutical composition may be further added with one or more kinds of active ingredients such as retinoids.

Dose of the medicament of the present invention is not particularly limited, and it can be suitably changed depending on various factors that should usually be taken into consideration, such as weight and age of patients, type and symptoms of disease, and route of administration. For example, in the case of oral administration, it can be used in the range of about 0.01 to 1,000 mg per day for adults.

EXAMPLES

Hereafter, the present invention will be more specifically explained with reference to examples. However, the scope of the present invention is not limited to the following examples. In the following examples, Me represents methyl group, and Et represents ethyl group.

Example 1

(1) 2,3,3a,4,5,6-Hexahydro-1H-phenalene

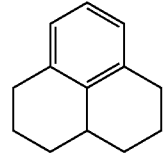

[Formula 2]

A solution of 2,3,3a,4,5,6-hexahydro-phenalene-1-one (2.00 g) in anhydrous tetrahydrofuran (70 ml) was cooled to 0° C., and slowly added with sodium borohydride (1.62 g) and aluminum chloride (2.85 g). The reaction mixture was refluxed by heating for 3 hours, then cooled to 0° C., and diluted with ethyl acetate. The reaction mixture was slowly added with ice until foaming ceased, and then the mixture was made to be at room temperature and stirred overnight. The reaction mixture was extracted with ethyl acetate, and the organic layer was washed successively with water and saturated brine, and dried over anhydrous sodium sulfate. The organic layer was concentrated under reduced pressure, and the resulting residue was purified by silica gel column chromatography (developing solvent: n-hexane) to obtain the title compound (1.47 g, yield: 80%).

$^1$H-NMR (400 MHz, CDCl$_3$): δ 1.26-1.40 (2H, m), 1.70-1.84 (2H, m), 1.85-2.00 (4H, m), 2.52-2.63 (1H, m), 2.78-2.82 (4H, m), 6.89 (1H, d, J=7.5 Hz), 7.02 (1H, t, J=7.5 Hz)

(2)
1-(5,6,6a,7,8,9-Hexahydro-4H-2-phenalenyl)ethanone

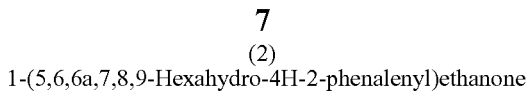

[Formula 3]

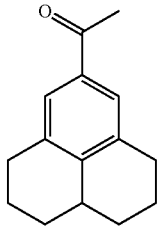

A suspension of aluminum chloride (0.250 g) in carbon disulfide (3 ml) was added with acetyl chloride (0.16 ml). The mixture was stirred at room temperature for 5 minutes, and then slowly added with 2,3,3a,4,5,6-hexahydro-1H-phenalene (0.250 g) dissolved in carbon disulfide (2 ml) at 0° C. The reaction mixture was stirred at 0° C. for 1 hour and at room temperature for 1 hour, and then poured into ice water, and the mixture was extracted with ethyl acetate. The organic layer was washed successively with water and saturated brine, and dried over anhydrous sodium sulfate. The organic layer was concentrated under reduced pressure, and the resulting residue was purified by silica gel column chromatography (developing solvent: ethyl acetate:n-hexane=1:500) to obtain (±)-1-(5,6,6a,7,8,9-hexahydro-4H-1-phenalenyl)ethanone (0.139 g, yield: 45%) and the title compound (0.135 g, yield: 43%).

$^1$H-NMR (400 MHz, CDCl$_3$): δ 1.26-1.40 (2H, m), 1.77-2.02 (6H, m), 2.55 (3H, s), 2.56-2.60 (1H, m), 2.82-2.87 (4H, m), 7.50 (2H, s)

(3)
5,6,6a,7,8,9-Hexahydro-4H-2-phenalenecarboxylic acid

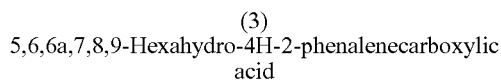

[Formula 4]

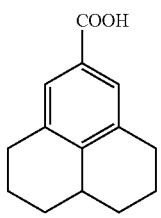

2.5 N Aqueous sodium hydroxide (9.2 ml) was cooled to 0° C., and slowly added with bromine (0.30 ml), and then the mixture was diluted with 1,4-dioxane (1.5 ml) to obtain a yellow solution. A solution of 1-(5,6,6a,7,8,9-hexahydro-4H-2-phenalenyl)ethanone (0.380 g) in water (5 ml) and 1,4-dioxane (10 ml) was cooled to 0° C., and slowly added with the yellow solution prepared above, and the mixture was stirred at 0° C. for 10 minutes and at room temperature for 1 hour. The reaction mixture was cooled to 0° C., and added with 10% aqueous sodium sulfite, then the mixture was made acidic with 2 N aqueous hydrochloric acid, and the mixture was extracted with chloroform. The organic layer was washed successively with water and saturated brine, and dried over anhydrous sodium sulfate. The organic layer was concentrated under reduced pressure, and the resulting residue was recrystallized from ethyl acetate-n-hexane to obtain the title compound (0.338 g, yield: 88%) as colorless needles (melting point: 208-209° C.). ° C.

$^1$H-NMR (400 MHz, CDCl$_3$): δ 1.26-1.41 (2H, m), 1.73-1.86 (2H, m), 1.88-2.05 (4H, m), 2.54-2.65 (1H, m), 2.82-2.88 (4H, m), 7.64 (2H, s)

(4) 5,6,6a,7,8,9-Hexahydro-4H-2-phenalenylamine

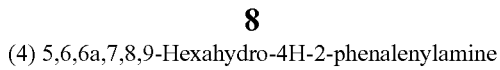

[Formula 5]

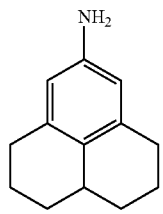

A solution of 5,6,6a,7,8,9-hexahydro-4H-2-phenalenecarboxylic acid (0.320 g) in anhydrous benzene (2 ml) was added with thionyl chloride (3 ml), and the mixture was refluxed by heating for 2 hours. The mixture was concentrated under reduced pressure, a solution of the resulting residue in anhydrous tetrahydrofuran (10 ml) was cooled to 0° C., and added with a solution of sodium azide (0.290 g) in water (1 ml), and the mixture was stirred at 0° C. for 30 minutes. The reaction mixture was added with saturated aqueous sodium hydrogencarbonate, and the mixture was extracted with diethyl ether. The organic layer was washed successively with water and saturated brine, and dried over anhydrous sodium sulfate. The organic layer was concentrated under reduced pressure, and the resulting residue was dissolved in acetic acid (7 ml) and water (3 ml), and the solution was refluxed overnight by heating. The reaction mixture was left to cool, then added with saturated aqueous sodium hydrogencarbonate and thereby made alkaline, and then the mixture was extracted with ethyl acetate. The organic layer was washed successively with water and saturated brine, and dried over anhydrous sodium sulfate. The organic layer was concentrated under reduced pressure, the resulting residue was dissolved in methanol (10 ml), the solution was added with concentrated hydrochloric acid (5 ml), and the mixture was refluxed by heating for 3 hours. The reaction mixture was left to cool, then diluted with diethyl ether, and extracted with 2 N aqueous hydrochloric acid. The aqueous layer was made alkaline with 2 N aqueous sodium hydroxide, and the mixture was extracted with diethyl ether. The organic layer was washed successively with water and saturated brine, and dried over anhydrous sodium sulfate. The organic layer was concentrated under reduced pressure, and the resulting residue was purified by silica gel column chromatography (developing solvent: ethyl acetate:n-hexane=1:50) to obtain the title compound (0.260 g, yield: 94%).

$^1$H-NMR (400 MHz, CDCl$_3$): δ 1.22-1.34 (2H, m), 1.66-1.80 (2H, m), 1.81-1.93 (4H, m), 2.40-2.54 (1H, m), 2.69-2.74 (4H, m), 3.43 (2H, br-s), 6.29 (2H, s)

(5) Methyl 4-[(5,6,6a,7,8,9-hexahydro-4H-2-phenalenyl)carbamoyl]benzoate

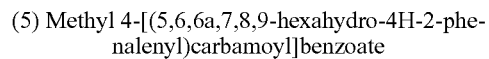

[Formula 6]

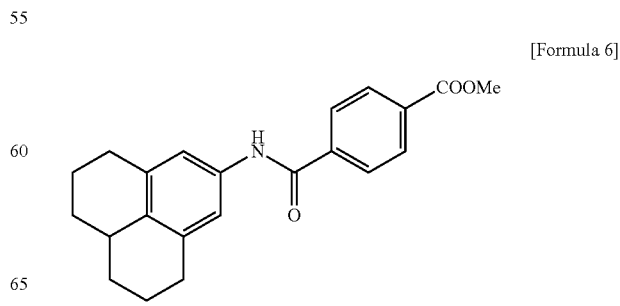

A solution of 5,6,6a,7,8,9-hexahydro-4H-2-phenalenylamine (0.260 g) in anhydrous benzene (10 ml) and pyridine (3 ml) was added with monomethyl terephthalate chloride (0.304 g), and the mixture was stirred at room temperature for 3 hours. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and then dried over anhydrous sodium sulfate. The organic layer was concentrated under reduced pressure, and the resulting residue was recrystallized from chloroform-n-hexane to obtain the title compound (0.460 g, yield: 95%) as colorless needles (melting point: 217-218° C.).

$^1$H-NMR (400 MHz, CDCl$_3$): δ 1.24-1.38 (2H, m), 1.70-1.84 (2H, m), 1.86-1.99 (4H, m), 2.49-2.59 (1H, m), 2.80-2.83 (4H, m), 3.96 (3H, s), 7.19 (2H, s), 7.77 (1H, br-s), 7.90 (2H, d, J=8.7 Hz), 8.12 (2H, d, J=8.7 Hz)

(6) 4-[(5,6,6a,7,8,9-Hexahydro-4H-2-phenalenyl)carbamoyl]benzoic acid

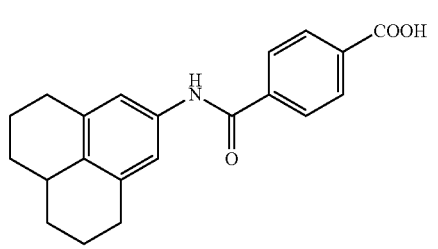

[Formula 7]

A suspension of methyl 4-[(5,6,6a,7,8,9-hexahydro-4H-2-phenalenyl)carbamoyl]benzoate (0.093 g) in ethanol (10 ml) was added with 2 N aqueous sodium hydroxide (3 ml), and the mixture was stirred at room temperature for 3 hours. The reaction mixture was made acidic with 2 N aqueous hydrochloric acid, and extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.080 g, yield: 90%) as colorless prisms (melting point: 283-284° C.).

$^1$H-NMR (400 MHz, CD$_3$OD): δ 1.24-1.37 (2H, m), 1.73-1.87 (2H, m), 1.88-2.02 (4H, m), 2.50-2.60 (1H, m), 2.78-2.83 (4H, m), 7.20 (2H, s), 7.98 (2H, d, J=8.7 Hz), 8.14 (2H, d, J=8.7 Hz)

$^1$H-NMR (400 MHz, DMSO-d$_6$): δ 1.21-1.30 (2H, m), 1.25-1.78 (2H, m), 1.81-1.94 (4H, m), 2.43-2.47 (1H, m), 2.73-2.76 (4H, m), 7.30 (2H, s), 8.01 (2H, d, J=8.6 Hz), 8.05 (2H, d, J=8.6 Hz), 10.15 (1H, s)

Example 2

(1) Methyl 4-[(5,6,6a,7,8,9-hexahydro-4H-2-phenalenyl)carboxamido]benzoate

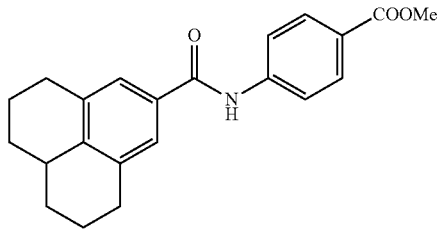

[Formula 8]

A suspension of 5,6,6a,7,8,9-hexahydro-4H-2-phenalenecarboxylic acid (0.338 g) in anhydrous benzene (7.5 ml) was added with thionyl chloride (2.5 ml), and the mixture was refluxed by heating for 4 hours. The reaction mixture was concentrated under reduced pressure, the resulting residue was dissolved in anhydrous benzene (3 ml) and pyridine (10 ml), the solution was added with methyl 4-aminobenzoate (0.259 g) and 4-dimethylaminopyridine (0.020 g), and the mixture was stirred for 15 hours. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: ethyl acetate:n-hexane=1:10) to obtain the title compound (0.478 g, yield: 88%). The compound was recrystallized from chloroform-n-hexane to obtain colorless needles (melting point: 187-189° C.).

$^1$H-NMR (400 MHz, CDCl$_3$): δ 1.26-1.41 (2H, m), 1.74-1.87 (2H, m), 1.89-2.61 (4H, m), 2.54-2.64 (1H, m), 2.83-2.88 (4H, m), 3.91 (3H, s), 7.39 (2H, s), 7.74 (2H, d, J=8.7 Hz), 7.95 (1H, br-s), 8.04 (2H, d, J=8.7 Hz)

(2) 4-[(5,6,6a,7,8,9-Hexahydro-4H-2-phenalenyl)carboxamido]benzoic acid

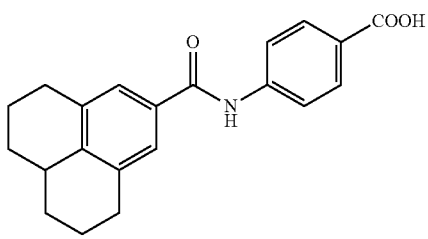

[Formula 9]

A suspension of methyl 4-[(5,6,6a,7,8,9-hexahydro-4H-2-phenalenyl)carboxamido]benzoate (0.385 g) in ethanol (25 ml) was added with 2 N aqueous sodium hydroxide (7.5 ml), and the mixture was stirred at 60° C. for 1 hour. The reaction mixture was left to cool and then made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.348 g, yield: 94%) as colorless needles (melting point: >300° C.).

$^1$H-NMR (400 MHz, CD$_3$OD): δ 1.28-1.41 (2H, m), 1.76-1.90 (2H, m), 1.91-2.07 (4H, m), 2.56-2.67 (1H, m), 2.88-2.90 (4H, m), 7.47 (2H, s), 7.83 (2H, d, J=8.7 Hz), 8.01 (2H, d, J=8.7 Hz)

$^1$H-NMR (400 MHz, DMSO-d$_6$): δ 1.21-1.34 (2H, m), 1.73-1.99 (6H, m), 2.55-2.66 (1H, m), 2.80-2.85 (4H, m), 7.49 (2H, s), 7.90 (4H, s), 10.33 (1H, s)

Example 3

(1) Methyl 2-fluoro-4-[(5,6,6a,7,8,9-hexahydro-4H-2-phenalenyl)carboxamido]benzoate

[Formula 10]

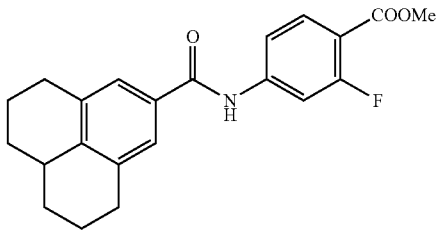

A suspension of 5,6,6a,7,8,9-hexahydro-4H-2-phenalenecarboxylic acid (0.150 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (3 ml) and pyridine (5 ml), the solution was added with methyl 2-fluoro-4-aminobenzoate (0.129 g) and 4-dimethylaminopyridine (one pellet), and the mixture was stirred overnight at room temperature. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: chloroform), and the substance eluted with chloroform was recrystallized from chloroform-n-hexane to obtain the title compound (0.227 g, yield: 89%) as colorless needles (melting point: 191-193° C.).

$^1$H-NMR (400 MHz, CDCl$_3$): δ 1.25-1.40 (2H, m), 1.73-1.87 (2H, m), 1.89-2.04 (4H, m), 2.53-2.62 (1H, m), 2.82-2.87 (4H, m), 3.92 (3H, s), 7.31 (1H, dd, J=12.9, 1.8 Hz), 7.37 (2H, s), 7.77 (1H, dd, J=12.9, 1.8 Hz), 7.94 (1H, t, J=8.9 Hz), 7.99 (1H, br-s)

(2) 2-Fluoro-4-[(5,6,6a,7,8,9-hexahydro-4H-2-phenalenyl)carboxamido]benzoic acid

[Formula 11]

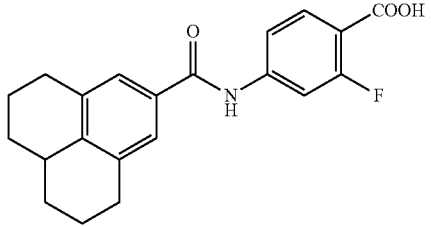

A suspension of methyl 2-fluoro-4-[(5,6,6a,7,8,9-hexahydro-4H-2-phenalenyl)carboxamido]benzoate (0.221 g) in ethanol (10 ml) was added with 2 N aqueous sodium hydroxide (2 ml), and the mixture was stirred at room temperature for 2 hours and at 60° C. for 1 hour. The reaction mixture was left to cool and then made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.190 g, yield: 90%) as colorless needles (melting point: >300° C.).

$^1$H-NMR (400 MHz, CD$_3$OD): δ 1.27-1.40 (2H, m), 1.76-1.88 (2H, m), 1.89-1.95 (2H, m), 1.96-2.06 (2H, m), 2.55-2.65 (1H, m), 2.84-2.89 (4H, m), 7.46 (2H, s), 7.53 (1H, dd, J=8.4, 2.1 Hz), 7.80 (1H, dd, J=13.5, 2.1 Hz), 7.91 (1H, t, J=8.4 Hz)

$^1$H-NMR (400 MHz, DMSO-d$_6$): δ 1.21-1.34 (2H, m), 1.74-1.80 (2H, m), 1.83-1.89 (2H, m), 1.92-1.99 (2H, m), 2.53-2.62 (1H, m), 2.80-2.85 (4H, m), 7.49 (2H, s), 7.65 (1H, dd, J=8.7, 2.1 Hz), 7.81-7.91 (2H, m), 10.51 (1H, s)

Example 4

(1) Methyl 2-chloro-4-[(5,6,6a,7,8,9-hexahydro-4H-2-phenalenyl)carboxamido]benzoate

[Formula 12]

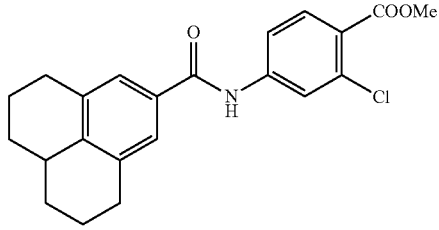

A suspension of 5,6,6a,7,8,9-hexahydro-4H-2-phenalenecarboxylic acid (0.150 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (3 ml) and pyridine (5 ml), the solution was added with methyl 2-chloro-4-aminobenzoate (0.142 g) and 4-dimethylaminopyridine (one pellet), and the mixture was stirred overnight at room temperature. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was recrystallized from chloroform-n-hexane to obtain the title compound (0.236 g, yield: 89%) as colorless needles (melting point: 163.5-165° C.).

$^1$H-NMR (400 MHz, CDCl$_3$): δ 1.27-1.41 (2H, m), 1.73-1.87 (2H, m), 1.89-2.04 (4H, m), 2.54-2.63 (1H, m), 2.83-2.88 (4H, m), 3.92 (3H, s), 7.38 (2H, m), 7.64 (1H, dd, J=8.4, 2.1 Hz), 7.84 (1H, d, J=2.1 Hz), 7.91 (1H, d, J=8.4 Hz), 7.91 (1H, br-s)

(2) 2-Chloro-4-[(5,6,6a,7,8,9-hexahydro-4H-2-phenalenyl)carboxamido]benzoic acid

[Formula 13]

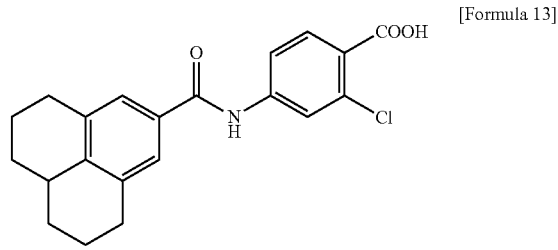

A suspension of methyl 2-chloro-4-[(5,6,6a,7,8,9-hexahydro-4H-2-phenalenyl)carboxamido]benzoate (0.210 g) in ethanol (10 ml) was added with 2 N aqueous sodium hydroxide (2 ml), and the mixture was stirred at room temperature for 3 hours and at 60° C. for 30 minutes. The reaction mixture was left to cool and then made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.163 g, yield: 81%) as colorless needles (melting point: 281-282° C.).

$^1$H-NMR (400 MHz, CD$_3$OD): δ 1.27-1.41 (2H, m), 1.76-1.88 (2H, m), 1.89-1.96 (2H, m), 1.97-2.06 (2H, m), 2.56-2.67 (1H, m), 2.85-2.90 (4H, m), 7.46 (2H, s), 7.71 (1H, dd, J=8.4, 2.1 Hz), 7.90 (1H, d, J=8.4 Hz), 8.02 (1H, d, J=2.1 Hz)

$^1$H-NMR (400 MHz, DMSO-d$_6$): δ 1.21-1.34 (2H, m), 1.73-1.80 (2H, m), 1.82-1.89 (2H, m), 1.92-1.99 (2H, m), 2.56-2.62 (1H, m), 2.80-2.85 (4H, m), 7.49 (2H, s), 7.80-7.87 (2H, m), 8.05 (1H, d, J=2.1 Hz), 10.43 (1H, s)

Example 5

(1) Methyl 2-hydroxy-4-[(5,6,6a,7,8,9-hexahydro-4H-2-phenalenyl)carboxamido]benzoate

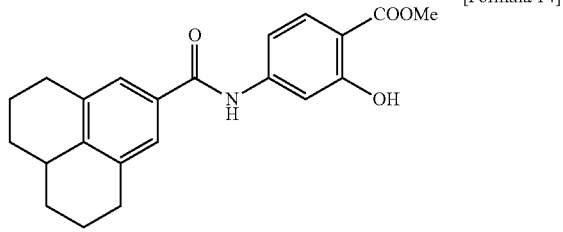

[Formula 14]

A suspension of 5,6,6a,7,8,9-hexahydro-4H-2-phenalenecarboxylic acid (0.150 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (3 ml) and pyridine (5 ml), the solution was added with methyl 2-hydroxy-4-aminobenzoate (0.128 g) and 4-dimethylaminopyridine (one pellet), and the mixture was stirred overnight at room temperature. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was recrystallized from chloroform-n-hexane to obtain the title compound (0.223 g, yield: 88%) as colorless needles (melting point: 198-199° C.).

$^1$H-NMR (400 MHz, CDCl$_3$): δ 1.27-1.41 (2H, m), 1.73-1.87 (2H, m), 1.89-2.04 (4H, m), 2.53-2.63 (1H, m), 2.83-2.88 (4H, m), 3.94 (3H, s), 7.24 (1H, dd, J=8.7, 2.1 Hz), 7.30 (1H, d, J=2.1 Hz), 7.37 (2H, s), 7.81 (1H, d, J=8.7 Hz), 7.85 (1H, br-s), 10.87 (1H, s)

(2) 2-Hydroxy-4-[(5,6,6a,7,8,9-hexahydro-4H-2-phenalenyl)carboxamido]benzoic acid

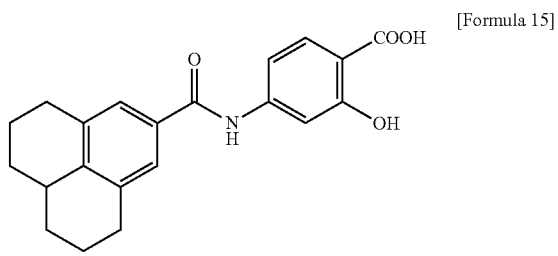

[Formula 15]

A suspension of methyl 2-hydroxy-4-[(5,6,6a,7,8,9-hexahydro-4H-2-phenalenyl)carboxamido]benzoate (0.208 g) in ethanol (10 ml) was added with 2 N aqueous sodium hydroxide (3 ml), and the mixture was stirred at room temperature overnight and at 60° C. for 2 hours. The reaction mixture was left to cool and then made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.179 g, yield: 90%) as colorless prisms (melting point: 267-267.5° C.).

$^1$H-NMR (400 MHz, CD$_3$OD): δ 1.27-1.40 (2H, m), 1.76-1.89 (2H, m), 1.90-1.96 (2H, m), 1.97-2.06 (2H, m), 2.55-2.66 (1H, m), 2.84-2.89 (4H, m), 7.22 (1H, dd, J=8.7, 2.1 Hz), 7.44 (2H, s), 7.47 (1H, d, J=2.1 Hz), 7.81 (1H, d, J=8.7 Hz)

$^1$H-NMR (400 MHz, DMSO-d$_6$): δ 1.15-1.33 (2H, m), 1.68-1.80 (2H, m), 1.82-1.89 (2H, m), 1.91-1.99 (2H, m), 2.53-2.61 (1H, m), 2.79-2.85 (4H, m), 7.32 (1H, dd, J=8.7, 2.1 Hz), 7.47 (2H, s), 7.53 (1H, d, J=2.1 Hz), 7.74 (1H, d, J=8.7 Hz), 10.29 (1H, s)

Example 6

(1) Methyl 2-methoxy-4-[(5,6,6a,7,8,9-hexahydro-4H-2-phenalenyl)carboxamido]benzoate

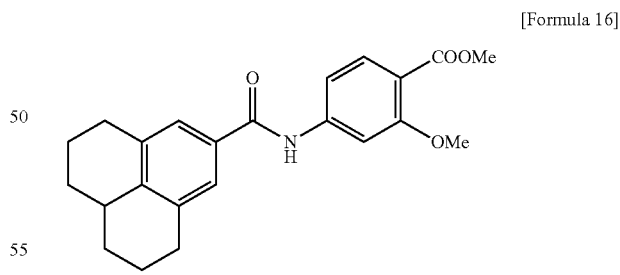

[Formula 16]

A suspension of 5,6,6a,7,8,9-hexahydro-4H-2-phenalenecarboxylic acid (0.100 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (5 ml), the solution was added with methyl 2-methoxy-4-aminobenzoate (0.092 g) and 4-dimethylaminopyridine (one pellet), and the mixture was stirred overnight at room temperature. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: ethyl acetate: n-hexane=1:5) to obtain the title compound (0.153 g, yield: 87%).

$^1$H-NMR (400 MHz, CDCl$_3$): δ 1.26-1.41 (2H, m), 1.73-1.87 (2H, m), 1.89-2.05 (4H, m), 2.54-2.63 (1H, m), 2.83-2.88 (4H, m), 3.88 (3H, s), 3.95 (3H, s), 6.96 (1H, dd, J=8.7, 2.1 Hz), 7.39 (2H, s), 7.83 (1H, d, J=2.1 Hz), 7.85 (1H, d, J=8.7 Hz), 7.99 (1H, br-s)

(2) 2-Methoxy-4-[(5,6,6a,7,8,9-hexahydro-4H-2-phenalenyl)carboxamido]benzoic acid

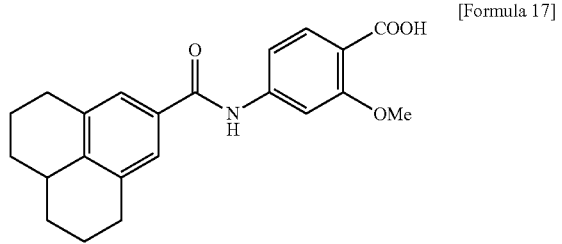

[Formula 17]

A suspension of methyl 2-hydroxy-4-[(5,6,6a,7,8,9-hexahydro-4H-2-phenalenyl)carboxamido]benzoate (0.150 g) in ethanol (10 ml) was added with 2 N aqueous sodium hydroxide (2 ml), and the mixture was stirred at room temperature for 2 hours and at 60° C. for 2 hours. The reaction mixture was left to cool and then made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.106 g, yield: 74%) as colorless needles (melting point: 206-208° C.).

$^1$H-NMR (400 MHz, CD$_3$OD): δ 1.26-1.41 (2H, m), 1.78-1.87 (2H, m), 1.88-1.96 (2H, m), 1.97-2.07 (2H, m), 2.55-2.67 (1H, m), 2.85-2.90 (4H, m), 3.94 (3H, s), 7.34 (1H, dd, J=8.4, 2.1 Hz), 7.47 (2H, s), 7.73 (1H, d, J=2.1 Hz), 7.84 (1H, d, J=8.4 Hz)

$^1$H-NMR (400 MHz, DMSO-d$_6$): δ 1.21-1.34 (2H, m), 1.74-1.80 (2H, m), 1.84-1.89 (2H, m), 1.92-1.99 (2H, m), 2.52-2.56 (1H, m), 2.80-2.85 (4H, m), 3.78 (3H, s), 7.35 (1H, d, J=8.1 Hz), 7.50 (2H, s), 7.56-7.62 (2H, m), 10.22 (1H, s)

Example 7

(1) Methyl 6-[(5,6,6a,7,8,9-hexahydro-4H-2-phenalenyl)carbamoyl]nicotinate

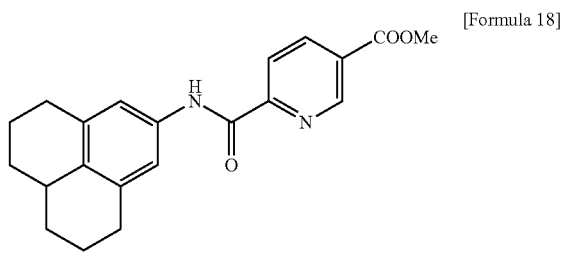

[Formula 18]

A suspension of pyridine-2,5-dicarboxylic acid 5-methyl ester (0.120 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (3 ml) and pyridine (1 ml), the solution was added with a solution of 5,6,6a,7,8,9-hexahydro-4H-2-phenalenylamine (0.118 g) in anhydrous benzene (2 ml), and the mixture was stirred at room temperature for 2 hours. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and then dried over anhydrous sodium sulfate. The organic layer was concentrated under reduced pressure, and the resulting residue was purified by silica gel column chromatography (developing solvent: ethyl acetate:n-hexane=1:15) to obtain the title compound (0.209 g, yield: 95%). The compound was recrystallized from chloroform-n-hexane to obtain pale yellow needles (melting point: 150-151° C.).

$^1$H-NMR (400 MHz, CDCl$_3$): δ 1.26-1.39 (2H, m), 1.72-1.85 (2H, m), 1.88-1.99 (4H, m), 2.52-2.59 (1H, m), 2.81-2.86 (4H, m), 4.00 (3H, s), 7.35 (2H, s), 8.36 (1H, d, J=8.4 Hz), 8.49 (1H, dd, J=8.4, 2.1 Hz), 9.18 (1H, d, J=2.1 Hz), 9.85 (1H, br-s)

(2) 6-[(5,6,6a,7,8,9-Hexahydro-4H-2-phenalenyl)carbamoyl]nicotinic acid

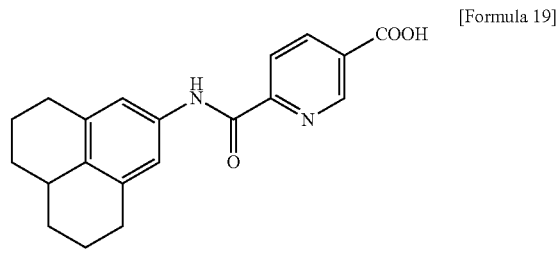

[Formula 19]

A suspension of methyl 6-[(5,6,6a,7,8,9-hexahydro-4H-2-phenalenyl)carbamoyl]nicotinate (0.194 g) in ethanol (10 ml) was added with 2 N aqueous sodium hydroxide (2 ml), and the mixture was stirred at room temperature for 2 hours. The reaction mixture was made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.161 g, yield: 87%) as pale yellow needles (melting point: 252-253° C.).

$^1$H-NMR (400 MHz, CDCl$_3$): δ 1.26-1.40 (2H, m), 1.72-1.86 (2H, m), 1.88-2.00 (4H, m), 2.51-2.61 (1H, m), 2.82-2.87 (4H, m), 7.36 (2H, s), 8.42 (1H, d, J=8.1 Hz), 8.58 (1H, dd, J=8.1, 2.1 Hz), 9.26 (1H, d, J=2.1 Hz), 9.88 (1H, s)

Example 8

(1) Methyl 6-[(5,6,6a,7,8,9-hexahydro-4H-2-phenalenyl)carboxamido]nicotinate

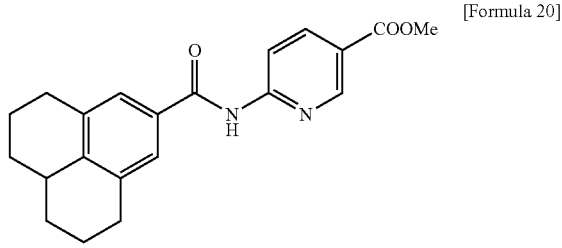

[Formula 20]

A suspension of 5,6,6a,7,8,9-hexahydro-4H-2-phenalenecarboxylic acid (0.150 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (3 ml) and pyridine (5 ml), the solution was added with methyl 6-amino-nicotinate (0.116 g) and 4-dimethylaminopyridine (one pellet), and the mixture was stirred overnight. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and dried over anhydrous sodium sulfate. The organic layer was concentrated under reduced pressure, and the resulting residue was purified by silica gel column chromatography (developing solvent: ethyl acetate:n-hexane=1:15) to obtain the title compound (0.196 g, yield: 81%). The compound was recrystallized from chloroform-n-hexane to obtain colorless needles (melting point: 148-150° C.).

$^1$H-NMR (400 MHz, CDCl$_3$): δ 1.28-1.42 (2H, m), 1.74-1.88 (2H, m), 1.90-2.05 (4H, m), 2.55-2.64 (1H, m), 2.84-2.89 (4H, m), 3.94 (3H, s), 7.46 (2H, s), 8.35 (1H, dd, J=8.7, 2.2 Hz), 8.48 (1H, d, J=8.7 Hz), 8.76 (1H, br-s), 8.93 (1H, d, J=2.2 Hz)

(2) 6-[(5,6,6a,7,8,9-Hexahydro-4H-2-phenalenyl)carboxamido]nicotinic acid

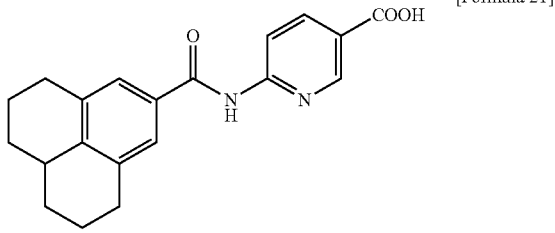

[Formula 21]

A suspension of methyl 6-[(5,6,6a,7,8,9-hexahydro-4H-2-phenalenyl)carboxamido]nicotinate (0.195 g) in ethanol (8 ml) was added with 2 N aqueous sodium hydroxide (2 ml), and the mixture was stirred at room temperature for 4 hours. The reaction mixture was made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethanol-chloroform to obtain the title compound (0.141 g, yield: 75%) as colorless powdery crystals (melting point: >300° C.).

$^1$H-NMR (400 MHz, DMSO-d$_3$): δ 1.20-1.34 (2H, m), 1.68-1.80 (2H, m), 1.82-1.99 (4H, m), 2.55-2.62 (1H, m), 2.78-2.83 (4H, m), 7.58 (2H, s), 8.30 (1H, s), 8.31 (1H, s), 8.88 (1H, d, J=1.8 Hz), 10.93 (1H, s)

Example 9

(1) Methyl 5-[(5,6,6a,7,8,9-hexahydro-4H-phenalenyl)carbamoyl]pyridine-2-carboxylate

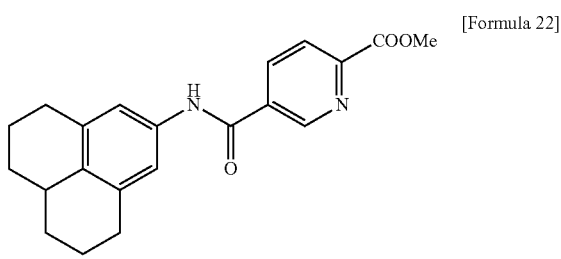

[Formula 22]

A suspension of pyridine-2,5-dicarboxylic acid 2-methyl ester (0.132 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (2 ml), the solution was added with a solution of 5,6,6a,7,8,9-hexahydro-4H-2-phenalenylamine (0.130 g) in anhydrous benzene (2 ml), and the mixture was stirred for 2 hours. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and dried over anhydrous sodium sulfate. The organic layer was concentrated under reduced pressure, and the resulting residue was purified by silica gel column chromatography (developing solvent: ethyl acetate:n-hexane=1:2) to obtain the title compound (0.224 g, yield: 92%). The compound was recrystallized from chloroform-n-hexane to obtain pale yellow needles (178-180° C.).

$^1$H-NMR (400 MHz, CDCl$_3$): δ 1.24-1.38 (2H, m), 1.70-1.84 (2H, m), 1.86-1.99 (4H, m), 2.50-2.57 (1H, m), 2.79-2.82 (4H, m), 4.04 (3H, s), 7.17 (2H, s), 7.86 (1H, br-s), 8.22 (1H, d, J=8.0 Hz), 8.32 (1H, dd, J=8.0 Hz, 2.3 Hz), 9.15 (1H, d, J=1.5 Hz)

(2) 5-[(5,6,6a,7,8,9-Hexahydro-4H-2-phenalenyl)carbamoyl]pyridine-2-carboxylic acid

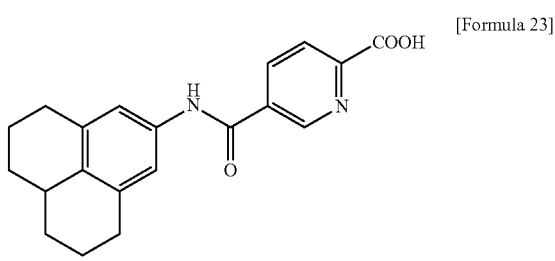

[Formula 23]

A suspension of methyl 5-[(5,6,6a,7,8,9-hexahydro-4H-2-phenalenyl)carbamoyl]pyridine-2-carboxylate (0.222 g) in ethanol (10 ml) was added with 2 N aqueous sodium hydroxide (2 ml), and the mixture was stirred at room temperature for 3 hours. The reaction mixture was made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.206 g, yield: 97%) as pale yellow needles (melting point: 239-240° C.).

$^1$H-NMR (400 MHz, DMSO-$d_3$): δ 1.14-1.28 (2H, m), 1.63-1.76 (2H, m), 1.78-1.83 (2H, m), 1.84-1.92 (2H, m), 2.40-2.42 (1H, m), 2.71-2.74 (4H, m), 7.27 (2H, s), 8.13 (1H, d, J=8.1 Hz), 8.40 (1H, dd, J=8.1, 2.1 Hz), 9.13 (1H, d, J=2.1 Hz), 10.32 (1H, s)

Example 10

(1) Methyl 5-[(5,6,6a,7,8,9-hexahydro-4H-2-phenalenyl)carboxamido]pyridine-2-carboxylate

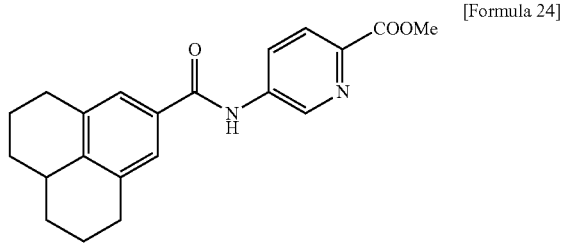

[Formula 24]

A suspension of 5,6,6a,7,8,9-hexahydro-4H-2-phenalenecarboxylic acid (0.120 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (3 ml) and pyridine (5 ml), the solution was added with methyl 5-amino-pyridine-2-carboxylate (0.093 g) and 4-dimethylaminopyridine (one pellet), and the mixture was stirred overnight. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and dried over anhydrous sodium sulfate. The organic layer was concentrated under reduced pressure, and the resulting residue was purified by silica gel column chromatography (developing solvent: ethyl acetate:n-hexane=1:2) to obtain the title compound (0.162 g, yield: 84%). The compound was recrystallized from chloroform-n-hexane to obtain colorless needles (melting point: 208-209° C.).

$^1$H-NMR (400 MHz, CDCl$_3$): δ 1.23-1.41 (2H, m), 1.74-1.88 (2H, m), 1.89-2.04 (4H, m), 2.56-2.64 (1H, m), 2.81-2.91 (4H, m), 4.00 (3H, s), 7.42 (2H, s), 8.09 (1H, br-s), 8.17 (1H, d, J=8.7 Hz), 8.57 (1H, dd, J=8.7, 2.7 Hz), 8.73 (1H, d, J=2.7 Hz)

(2) 5-[(5,6,6a,7,8,9-Hexahydro-4H-2-phenalenyl)carboxamido]pyridine-2-carboxylic acid

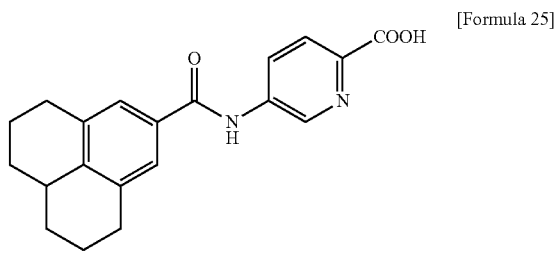

[Formula 25]

A suspension of methyl 5-[(5,6,6a,7,8,9-hexahydro-4H-2-phenalenyl)carboxamido]pyridine-2-carboxylate (0.158 g) in ethanol (10 ml) was added with 2 N aqueous sodium hydroxide (2 ml), and the mixture was stirred at room temperature for 3 hours. The reaction mixture was made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethanol to obtain the title compound (0.125 g, yield: 82%) as pale yellow powdery crystals (melting point: 219-220° C.).

$^1$H-NMR (400 MHz, DMSO-$d_3$): δ 1.19-1.32 (2H, m), 1.71-1.78 (2H, m), 1.82-1.87 (2H, m), 1.88-1.97 (2H, m), 2.53-2.60 (1H, m), 2.78-2.83 (4H, m), 7.50 (2H, s), 8.04 (1H, d, J=8.4 Hz), 8.37 (1H, dd, J=8.4, 2.7 Hz), 9.01 (1H, d, J=2.7 Hz), 10.55 (1H, s)

Example 11

(1) Methyl 5-[(5,6,6a,7,8,9-hexahydro-4H-2-phenalenyl)carbamoyl]thiophene-2-carboxylate

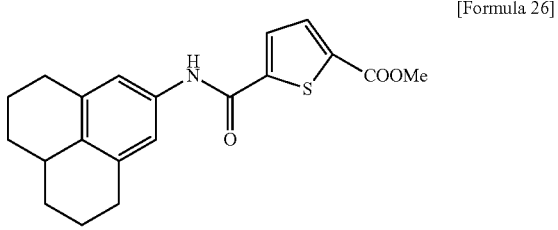

[Formula 26]

A suspension of thiophene-2,5-dicarboxylic acid 2-methyl ester (0.083 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (2 ml), the solution was added with a solution of 5,6,6a,7,8,9-hexahydro-4H-2-phenalenylamine (0.080 g) in anhydrous benzene (2 ml), and the mixture was stirred for 3 hours. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and dried over anhydrous sodium sulfate. The organic layer was concentrated under reduced pressure, and the resulting residue was recrystallized from chloroform-n-hexane to obtain the title compound (0.111 g, yield: 73%) as colorless needles (melting point: 221-222° C.).

$^1$H-NMR (400 MHz, CDCl$_3$): δ 1.24-1.38 (2H, m), 1.70-1.86 (2H, m), 1.88-1.99 (4H, m), 2.48-2.59 (1H, m), 2.78-2.83 (4H, m), 3.92 (3H, s), 7.14 (2H, s), 7.53 (1H, d, J=3.9 Hz), 7.58 (1H, br-s), 7.76 (1H, d, J=3.9 Hz)

(2) 5-[(5,6,6a,7,8,9-Hexahydro-4H-2-phenalenyl)carbamoyl]thiophene-2-carboxylic acid

[Formula 27]

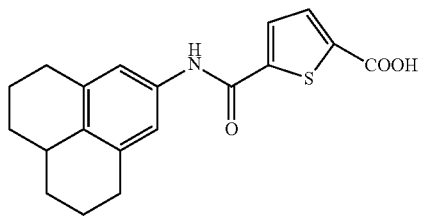

A suspension of methyl 5-[(5,6,6a,7,8,9-hexahydro-4H-2-phenalenyl)carbamoyl]thiophene-2-carboxylate (0.110 g) in ethanol (10 ml) was added with 2 N aqueous sodium hydroxide (1 ml), and the mixture was stirred at room temperature for 4 hours. The reaction mixture was made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.093 g, yield: 89%) as pale yellow powdery crystals (melting point: 281-283° C.).

$^1$H-NMR (400 MHz, DMSO-d$_3$): δ 1.18-1.27 (2H, m), 1.66-1.76 (2H, m), 1.77-1.92 (4H, m), 2.44-2.45 (1H, m), 2.71-2.73 (4H, m), 7.22 (2H, s), 7.26 (1H, d, J=4.2 Hz), 7.95 (1H, d, J=4.2 Hz), 10.17 (1H, s)

Example 12

(1) Methyl 5-[(5,6,6a,7,8,9-hexahydro-4H-2-phenalenyl)carboxamido]thiophene-2-carboxylate

[Formula 28]

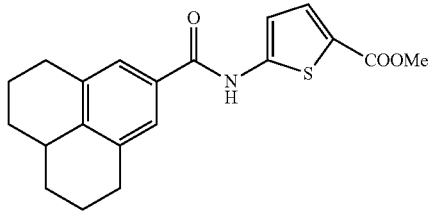

A suspension of 5,6,6a,7,8,9-hexahydro-4H-2-phenalenecarboxylic acid (0.100 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (2 ml), the solution was added with methyl 5-amino-thiophene-2-carboxylate (0.076 g) and 4-dimethylaminopyridine (one pellet), and the mixture was stirred overnight. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and dried over anhydrous sodium sulfate. The organic layer was concentrated under reduced pressure, and the resulting residue was purified by silica gel column chromatography (developing solvent: ethyl acetate:n-hexane=1:15) to obtain the title compound (0.094 g, yield: 57%). The compound was recrystallized from chloroform-n-hexane to obtain colorless needles (melting point: 188-189° C.).

$^1$H-NMR (400 MHz, CDCl$_3$): δ 1.34 (2H, td, J=12.0, 3.9 Hz), 1.72-1.85 (2H, m), 1.87-2.04 (4H, m), 2.52-2.63 (1H, m), 2.80-2.85 (4H, m), 3.87 (3H, s), 6.75 (1H, d, J=4.2 Hz), 7.41 (2H, s), 7.64 (1H, d, J=4.2 Hz), 8.94 (1H, br-s)

(2) 5-[(5,6,6a,7,8,9-Hexahydro-4H-2-phenalenyl)carboxamido]thiophene-2-carboxylic acid

[Formula 29]

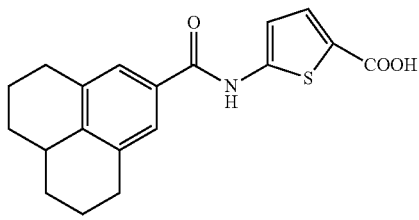

A suspension of methyl 5-[(5,6,6a,7,8,9-hexahydro-4H-2-phenalenyl)carboxamido]thiophene-2-carboxylate (0.071 g) in ethanol (5 ml) was added with 2 N aqueous sodium hydroxide (1 ml), and the mixture was stirred at 60° C. for 2 hours. The reaction mixture was made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.043 g, yield: 63%) as colorless powdery crystals (melting point: 259-261° C.).

$^1$H-NMR (400 MHz, DMSO-d$_3$): δ 1.20-1.32 (2H, m), 1.71-1.78 (2H, m), 1.79-1.87 (2H, m), 1.89-1.98 (2H, m), 2.53-2.61 (1H, m), 2.78-2.83 (4H, m), 6.90 (1H, d, J=4.2 Hz), 7.52 (2H, s), 7.54 (1H, d, J=4.2 Hz), 11.74 (1H, s)

Example 13

4-[(5,6,6a,7,8,9-Hexahydro-4H-2-phenalenyl)sulfamoyl]benzoic acid

[Formula 30]

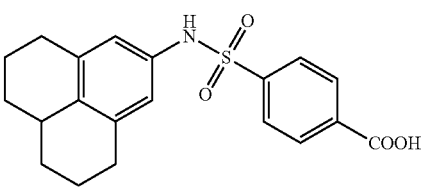

5,6,6a,7,8,9-Hexahydro-4H-2-phenalenylamine (0.130 g) was dissolved in pyridine (5 ml) and anhydrous benzene (2 ml), the solution was added with 4-chlorosulfonylbenzoic acid (0.161 g) and 4-dimethylaminopyridine (one pellet), and the mixture was stirred overnight at room temperature. The reaction mixture was made to be at 60° C., stirred for 3 hours, left to cool, then added with 2 N aqueous hydrochloric acid and thereby made acidic, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.194 g, yield: 75%) as brown needles (melting point: 266-268° C.).

$^1$H-NMR (400 MHz, DMSO-d$_3$): δ 1.06-1.18 (2H, m), 1.54-1.66 (2H, m), 1.70-1.74 (2H, m), 1.78-1.83 (2H, m), 2.32-2.43 (1H, m), 2.55-2.59 (4H, m), 6.58 (2H, s), 7.84 (2H, d, J=8.1 Hz), 8.05 (2H, d, J=8.1 Hz), 10.14 (1H, s)

Example 14

(1) (±)-3a-Methyl-2,3,3a,4-tetrahydro-1H-phenalene

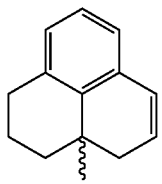

[Formula 31]

A solution of (±)-3a-methyl-2,3,3a,4,5,6-hexahydro-1-phenalenone (2.14 g) in anhydrous tetrahydrofuran (70 ml) was cooled to 0° C., and slowly added with sodium borohydride (1.62 g) and aluminum chloride (2.85 g). The reaction mixture was refluxed by heating for 3 hours, then cooled to 0° C., and diluted with ethyl acetate. The mixture was slowly added with ice until foaming ceased, and then the mixture was made to be at room temperature and stirred overnight. The reaction mixture was extracted with ethyl acetate, and the organic layer was washed successively with water and saturated brine, and dried over anhydrous sodium sulfate. The organic layer was concentrated under reduced pressure, and the resulting residue was purified by silica gel column chromatography (developing solvent: n-hexane) to obtain the title compound (1.83 g, yield: 97%).

$^1$H-NMR (400 MHz, CDCl$_3$): δ 1.16 (3H, s), 1.64 (1H, td, J=13.1, 3.4 Hz), 1.74 (1H, dt, J=12.8, 3.4 Hz), 1.79-1.89 (1H, m), 1.92-2.04 (1H, m), 2.10 (1H, dd, J=17.1, 6.3 Hz), 2.27 (1H, dt, J=17.1, 2.7 Hz), 2.77-2.83 (2H, m), 5.89-5.95 (1H, m), 6.45 (1H, dd, J=9.6, 3.0 Hz), 6.85 (1H, d, J=7.5 Hz), 6.92 (1H, d, J=7.5 Hz), 7.03 (1H, t, J=7.5 Hz)

(2) 3a-Methyl-2,3,3a,4,5,6-hexahydro-1H-phenalene

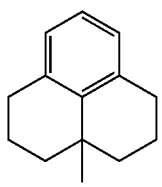

[Formula 32]

3a-Methyl-2,3,3a,4-tetrahydro-1H-phenalene (1.83 g) was dissolved in ethanol (12 ml), the solution was added with 10% palladium/carbon (0.183 g), and the mixture was stirred for 6 hours under a hydrogen flow. The reaction mixture was filtered through Celite, then the solvent of the filtrate was concentrated under reduced pressure, and the resulting residue was purified by silica gel column chromatography using a small amount of silica gel (developing solvent: n-hexane) to obtain the title compound (1.74 g, yield: 94%).

$^1$H-NMR (400 MHz, CDCl$_3$): δ 1.17 (3H, s), 1.51 (2H, td, J=13.1, 5.1 Hz), 1.66 (2H, dt, J=13.1, 4.1 Hz), 1.74-1.86 (2H, m), 1.98-2.14 (2H, m), 2.79 (2H, dt, J=17.1, 8.6 Hz), 2.91 (2H, ddd, J=17.1, 8.1, 3.5 Hz), 6.88 (2H, dd, J=7.5, 0.8 Hz), 7.00 (1H, dd, J=8.1, 6.6 Hz)

(3) 1-(6a-Methyl-5,6,6a,7,8,9-hexahydro-4H-2-phenalenyl)ethanone

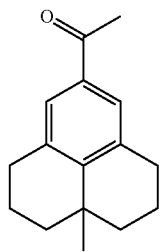

[Formula 33]

A suspension of aluminum chloride (1.62 g) in carbon disulfide (25 ml) was added with acetyl chloride (1.00 ml) at −10° C. The mixture was stirred at −10° C. for 20 minutes, and then slowly added with 3a-methyl-2,3,3a,4,5,6-hexahydro-1H-phenalene (1.74 g) dissolved in carbon disulfide (15 ml), and the temperature of the mixture was gradually elevated to room temperature. The reaction mixture was stirred at room temperature for 30 minutes, and then poured into ice water, and the mixture was extracted with ethyl acetate. The organic layer was washed successively with water and saturated brine, and dried over anhydrous sodium sulfate. The organic layer was concentrated under reduced pressure, and the resulting residue was purified by silica gel column chromatography (developing solvent: ethyl acetate: n-hexane=1:500) to obtain W-1-(6a-methyl-5,6,6a,7,8,9-hexahydro-4H-1-phenalenyl)ethanone (1.63 g, yield: 77%) and the title compound (0.465 g, yield: 22%). The compound was recrystallized from n-hexane to obtain colorless prisms (melting point: 100-101.5° C.).

$^1$H-NMR (400 MHz, CDCl$_3$): δ 1.17 (3H, s), 1.51 (2H, td, J=13.0, 4.8 Hz), 1.70 (2H, dt, J=13.0, 4.1 Hz), 1.78-1.89 (2H, m), 1.99-2.15 (2H, m), 2.55 (3H, s), 2.82 (2H, dt, J=17.1, 8.6 Hz), 2.97 (2H, ddd, J=17.3, 7.9, 3.3 Hz), 7.48 (2H, s)

(4) 6a-Methyl-5,6,6a,7,8,9-hexahydro-4H-2-phenalenecarboxylic acid

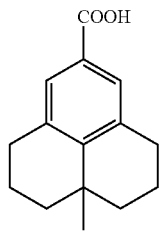

[Formula 34]

2.5 N Aqueous sodium hydroxide (9.3 ml) was cooled to 0° C., slowly added with bromine (0.30 ml), and then diluted with 1,4-dioxane (10 ml) to obtain a yellow solution. A solution of 1-(6a-methyl-5,6,6a,7,8,9-hexahydro-4H-2-phenalenyl)ethanone (0.409 g) in water (5 ml) and 1,4-dioxane (10 ml) was cooled to 0° C., and slowly added with the yellow solution prepared above, and the mixture was stirred at 0° C. for 30 minutes and at room temperature for 1 hour. The reaction mixture was cooled to 0° C., and added with 10% aqueous sodium sulfite, the mixture was made acidic with 2 N aqueous hydrochloric acid, and the mixture was extracted with chloroform. The organic layer was washed successively with water and saturated brine, and dried over anhydrous sodium sulfate. The organic layer was concentrated under reduced pressure, and the resulting residue was recrystallized from ethyl acetate-n-hexane to obtain the title compound (0.333 g, yield: 81%) as colorless needles (melting point: 213-215° C.).

$^1$H-NMR (400 MHz, CDCl$_3$): δ 1.17 (3H, s), 1.52 (2H, td, J=13.1, 5.1 Hz), 1.70 (2H, dt, J=13.1, 4.1 Hz), 1.78-1.89 (2H, m), 1.99-2.15 (2H, m), 2.84 (2H, dt, J=17.3, 8.6 Hz), 2.97 (2H, ddd, J=17.3, 8.1, 3.6 Hz), 7.62 (2H, s)

(5) 6a-Methyl-5,6,6a,7,8,9-hexahydro-4H-2-phenalenylamine

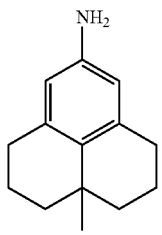

[Formula 35]

A solution of 6a-methyl-5,6,6a,7,8,9-hexahydro-4H-2-phenalenecarboxylic acid (0.165 g) in anhydrous benzene (3 ml) was added with thionyl chloride (1 ml), and the mixture was refluxed by heating for 2 hours. The reaction mixture was concentrated under reduced pressure, a solution of the resulting residue in anhydrous tetrahydrofuran (5 ml) was cooled to 0° C., and added with a solution of sodium azide (0.140 g) in water (0.5 ml), and the mixture was stirred at 0° C. for 30 minutes. The reaction mixture was added with saturated aqueous sodium hydrogencarbonate, and the mixture was extracted with diethyl ether. The organic layer was washed successively with water and saturated brine, and dried over anhydrous sodium sulfate. The organic layer was concentrated under reduced pressure, the resulting residue was dissolved in acetic acid (5 ml) and water (2 ml), and the solution was refluxed overnight by heating. The reaction mixture was left to cool and then added with saturated aqueous sodium hydrogencarbonate and thereby made alkaline, and then the mixture was extracted with ethyl acetate. The organic layer was washed successively with water and saturated brine, and dried over anhydrous sodium sulfate. The organic layer was concentrated under reduced pressure, the resulting residue was dissolved in methanol (5 ml), the solution was added with concentrated hydrochloric acid (3 ml), and the mixture was refluxed by heating for 3 hours. The reaction mixture was left to cool and then made alkaline with 10% aqueous sodium carbonate, and the mixture was extracted with diethyl ether. The organic layer was washed successively with water and saturated brine, and dried over anhydrous sodium sulfate. The organic layer was concentrated under reduced pressure, and the resulting residue was purified by silica gel column chromatography (developing solvent: ethyl acetate:n-hexane=1: 50) to obtain the title compound (0.138 g, yield: 96%).

$^1$H-NMR (400 MHz, CDCl$_3$): δ 1.13 (3H, s), 1.46 (2H, td, J=12.9, 5.1 Hz), 1.62 (2H, dt, J=12.9, 4.1 Hz), 1.71-1.82 (2H, m), 1.94-2.10 (2H, m), 2.69 (2H, dt, J=17.1, 8.6 Hz), 2.81 (2H, ddd, J=17.4, 8.0, 3.5 Hz), 3.40 (2H, br-s), 6.27 (2H, s)

(6) Methyl 4-[(6a-methyl-5,6,6a,7,8,9-hexahydro-4H-2-phenalenyl)carbamoyl]benzoate

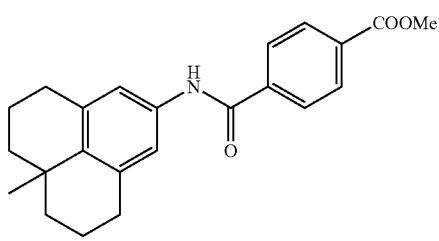

[Formula 36]

A solution of 6a-methyl-5,6,6a,7,8,9-hexahydro-4H-2-phenalenylamine (0.138 g) in anhydrous benzene (5 ml) and pyridine (2 ml) was added with monomethyl terephthalate chloride (0.177 g), and the mixture was stirred at room temperature for 2 hours. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and then dried over anhydrous sodium sulfate. The organic layer was concentrated under reduced pressure, and the resulting residue was recrystallized from chloroform-n-hexane to obtain the title compound (0.205 g, yield: 82%) as colorless needles (melting point: 217-218° C.).

$^1$H-NMR (400 MHz, CDCl$_3$): δ 1.16 (3H, s), 1.50 (2H, td, J=12.9, 5.1 Hz), 1.68 (2H, dt, J=12.9, 4.1 Hz), 1.76-1.87 (2H, m), 1.98-2.15 (2H, m), 2.79 (2H, dt, J=17.4, 8.7 Hz), 2.92 (2H, ddd, J=17.3, 7.9, 3.4 Hz), 3.96 (3H, s), 7.18 (2H, s), 7.69 (1H, br-s), 7.89 (2H, d, J=8.4 Hz), 8.13 (2H, d, J=8.4 Hz)

(7) 4-[(6a-Methyl)-5,6,6a,7,8,9-hexahydro-4H-2-phenalenyl)carbamoyl]benzoic acid

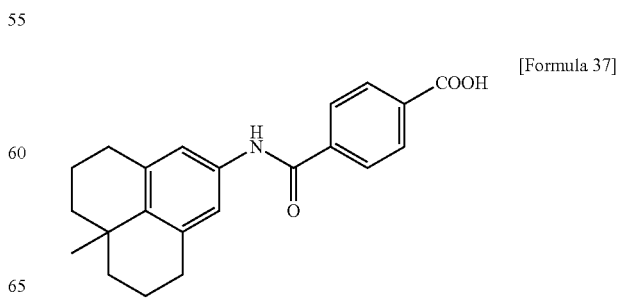

[Formula 37]

A suspension of methyl 4-[(6a-methyl-5,6,6a,7,8,9-hexahydro-4H-2-phenalenyl)carbamoyl]benzoate (0.200 g) in ethanol (10 ml) was added with 2 N aqueous sodium hydroxide (3 ml), and the mixture was stirred at room temperature for 3 hours. The reaction mixture was made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethanol-water to obtain the title compound (0.167 g, yield: 87%) as colorless needles (melting point: 282-283° C.).

$^1$H-NMR (400 MHz, CD$_3$OD): δ 1.17 (3H, s), 1.49 (2H, td, J=12.9, 4.1 Hz), 1.70 (2H, dt, J=12.9, 4.1 Hz), 1.76-1.87 (2H, m), 2.02-2.18 (2H, m), 2.78 (2H, dt, J=17.3, 8.6 Hz), 2.88 (2H, ddd, J=17.1, 7.8, 3.3 Hz), 7.18 (2H, s), 7.97 (2H, d, J=8.4 Hz), 8.12 (2H, d, J=8.4 Hz)

$^1$H-NMR (400 MHz, DMSO-d$_6$): δ 1.11 (3H, s), 1.42 (2H, td, J=12.8, 4.9 Hz), 1.64 (2H, dt, J=12.8, 4.0 Hz), 1.71-1.80 (2H, m), 1.93-2.09 (2H, m), 2.72 (2H, dt, J=17.4, 8.7 Hz), 2.85 (2H, ddd, J=17.1, 7.8, 3.0 Hz), 7.28 (2H, s), 8.01 (2H, d, J=8.4 Hz), 8.05 (2H, d, J=8.4 Hz), 10.13 (1H, s)

Example 15

(1) Methyl 4-[(6a-methyl-5,6,6a,7,8,9-hexahydro-4H-2-phenalenyl)carboxamido]benzoate

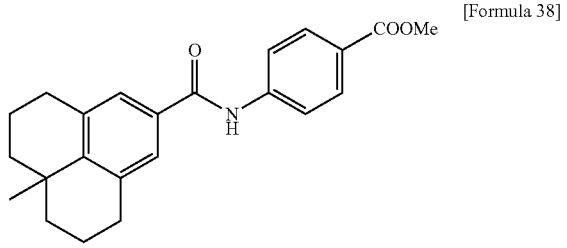

[Formula 38]

A suspension of 6a-methyl-5,6,6a,7,8,9-hexahydro-4H-2-phenalenecarboxylic acid (0.160 g) in anhydrous benzene (5 ml) was added with thionyl chloride (2 ml), and the mixture was refluxed by heating for 4 hours. The reaction mixture was concentrated under reduced pressure, the resulting residue was dissolved in anhydrous benzene (4 ml) and pyridine (2 ml), the solution was added with methyl 4-aminobenzoate (0.126 g) and 4-dimethylaminopyridine (0.010 g), and the mixture was stirred for 16 hours. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: ethyl acetate:n-hexane=1:15) to obtain the title compound (0.160 g, yield: 63%). The compound was recrystallized from chloroform-n-hexane to obtain colorless needles (melting point: 176-178° C.).

$^1$H-NMR (400 MHz, CDCl$_3$): δ 1.17 (3H, s), 1.52 (2H, td, J=12.9, 4.8 Hz), 1.71 (2H, dt, J=12.9, 4.2 Hz), 1.78-1.90 (2H, m), 1.99-2.16 (2H, m), 2.87 (2H, dt, J=17.4, 8.7 Hz), 2.98 (2H, ddd, J=17.4, 7.8, 3.3 Hz), 3.91 (3H, s), 7.38 (2H, s), 7.73 (2H, d, J=8.9 Hz), 7.94 (1H, br-s), 8.04 (2H, d, J=8.9 Hz)

(2) 4-[(6a-Methyl-5,6,6a,7,8,9-hexahydro-4H-2-phenalenyl)carboxamido]benzoic acid

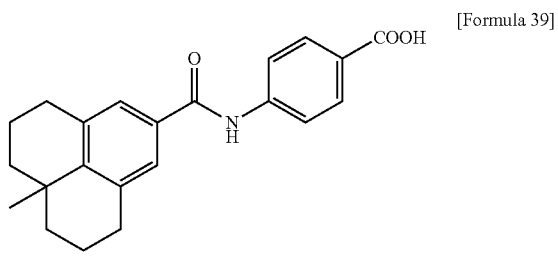

[Formula 39]

A suspension of methyl 4-[(6a-methyl-5,6,6a,7,8,9-hexahydro-4H-2-phenalenyl)carboxamido]benzoate (0.158 g) in ethanol (10 ml) was added with 2 N aqueous sodium hydroxide (3 ml), and the mixture was stirred at room temperature for 4 hours. The reaction mixture was made acidic with 2 N aqueous hydrochloric acid, and the mixture was extracted with chloroform. The organic layer was washed with saturated brine, dried over anhydrous sodium sulfate, and then concentrated under reduced pressure, and the resulting residue was recrystallized from ethyl acetate-n-hexane to obtain the title compound (0.134 g, yield: 88%) as colorless prisms (melting point: 283.5-285° C.).

$^1$H-NMR (400 MHz, CD$_3$OD): δ 1.20 (3H, s), 1.53 (2H, td, J=13.0, 5.0 Hz), 1.74 (2H, dt, J=13.0, 4.1 Hz), 1.80-1.91 (2H, m), 2.04-2.21 (2H, m), 2.86 (2H, dt, J=17.3, 8.6 Hz), 3.00 (2H, ddd, J=17.4, 7.8, 3.3 Hz), 7.45 (2H, s), 7.82 (2H, d, J=9.0 Hz), 8.00 (2H, d, J=9.0 Hz)

$^1$H-NMR (400 MHz, DMSO-d$_6$): δ 1.14 (3H, s), 1.45 (2H, td, J=12.8, 4.8 Hz), 1.69 (2H, dt, J=12.8, 3.8 Hz), 1.74-1.83 (2H, m), 1.95-2.11 (2H, m), 2.81 (2H, dt, J=17.4, 8.7 Hz), 2.96 (2H, ddd, J=17.0, 7.8, 2.9 Hz), 7.45 (2H, s), 7.87 (2H, d, J=8.9 Hz), 7.92 (2H, d, J=8.9 Hz), 10.34 (1H, s)

Example 16

(1) Methyl 2-fluoro-4-[(6a-methyl-5,6,6a,7,8,9-hexahydro-4H-2-phenalenyl)carboxamido]benzoate

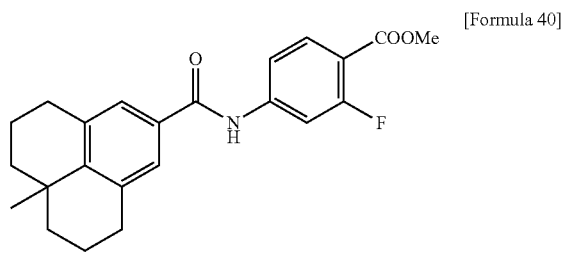

[Formula 40]

A suspension of 6a-methyl-5,6,6a,7,8,9-hexahydro-4H-2-phenalenecarboxylic acid (0.150 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (5 ml), the solution was added with methyl 2-fluoro-4-aminobenzoate (0.121 g) and 4-dimethylaminopyridine (one pellet), and the mixture was stirred overnight at room temperature. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: ethyl acetate: n-hexane=1:15) to obtain the title compound (0.226 g, yield: 91%). The compound was recrystallized from chloroform-n-hexane to obtain colorless needles (melting point: 178-180° C.).

$^1$H-NMR (400 MHz, CDCl$_3$): δ 1.17 (3H, s), 1.51 (2H, td, J=12.9, 5.1 Hz), 1.72 (2H, dt, J=12.9, 4.1 Hz), 1.80-1.91 (2H, m), 2.01-2.17 (2H, m), 2.85 (2H, dt, J=17.3, 8.6 Hz), 2.99 (2H, ddd, J=17.6, 7.8, 3.5 Hz), 3.92 (3H, s), 7.30 (1H, dd, J=8.4, 2.1 Hz), 7.36 (2H, s), 7.77 (1H, dd, J=13.1, 2.1 Hz), 7.91 (1H, br-s), 7.95 (1H, t, J=8.4 Hz)

(2) 2-Fluoro-4-[(6a-methyl-5,6,6a,7,8,9-hexahydro-4H-2-phenalenyl)carboxamido]benzoic acid

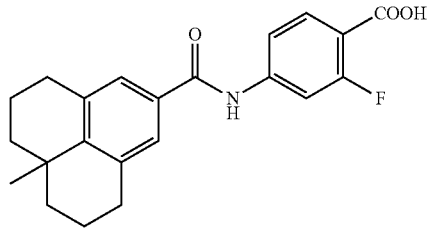

[Formula 41]

A suspension of methyl 2-fluoro-4-[(6a-methyl-5,6,6a,7,8,9-hexahydro-4H-2-phenalenyl)carboxamido]benzoate (0.222 g) in ethanol (10 ml) was added with 2 N aqueous sodium hydroxide (2 ml), and the mixture was stirred at room temperature for 2 hours and at 60° C. for 30 minutes. The reaction mixture was left to cool and then made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.173 g, yield: 81%) as colorless prisms (melting point: 276-278° C.).

$^1$H-NMR (400 MHz, CD$_3$OD): δ 1.19 (3H, s), 1.52 (2H, td, J=12.9, 5.1 Hz), 1.73 (2H, dt, J=12.9, 4.1 Hz), 1.79-1.91 (2H, m), 2.01-2.20 (2H, m), 2.86 (2H, dt, J=17.3, 8.7 Hz), 3.00 (2H, ddd, J=17.4, 8.0, 3.5 Hz), 7.45 (2H, s), 7.53 (1H, dd, J=8.7, 2.1 Hz), 7.80 (1H, dd, J=13.7, 2.1 Hz), 7.91 (1H, t, J=8.7 Hz)

$^1$H-NMR (400 MHz, DMSO-d$_6$): δ 1.14 (3H, s), 1.45 (2H, td, J=12.9, 5.1 Hz), 1.67 (2H, dt, J=12.9, 3.9 Hz), 1.74-1.85 (2H, m), 1.95-2.11 (2H, m), 2.82 (2H, dt, J=17.3, 8.7 Hz), 2.96 (2H, ddd, J=17.3, 7.8, 3.3 Hz), 7.45 (2H, s), 7.63 (1H, d, J=8.7 Hz), 7.79-7.91 (2H, m), 10.50 (1H, s)

Example 17

(1) Methyl 2-chloro-4-[(6a-methyl-5,6,6a,7,8,9-hexahydro-4H-2-phenalenyl)carboxamido]benzoate

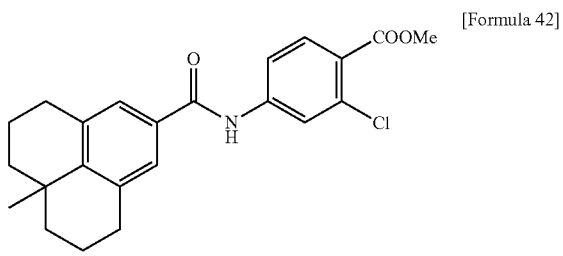

[Formula 42]

A suspension of 6a-methyl-5,6,6a,7,8,9-hexahydro-4H-2-phenalenecarboxylic acid (0.150 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (5 ml), the solution was added with methyl 2-chloro-4-aminobenzoate (0.133 g) and 4-dimethylaminopyridine (one pellet), and the mixture was stirred overnight at room temperature. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: ethyl acetate: n-hexane=1:15) to obtain the title compound (0.249 g, yield: 96%). The compound was recrystallized from chloroform-n-hexane to obtain colorless needles (melting point: 157-158° C.).

$^1$H-NMR (400 MHz, CDCl$_3$): δ 1.16 (3H, s), 1.51 (2H, td, J=12.9, 4.8 Hz), 1.71 (2H, dt, J=12.9, 4.1 Hz), 1.78-1.89 (2H, m), 1.99-2.15 (2H, m), 2.82 (2H, dt, J=17.1, 8.6 Hz), 2.96 (2H, ddd, J=17.3, 7.8, 3.2 Hz), 3.91 (3H, s), 7.36 (2H, s), 7.64 (1H, dd, J=8.7, 2.1 Hz), 7.84 (1H, d, J=2.1 Hz), 7.89 (1H, d, J=8.7 Hz), 7.98 (1H, br-s)

(2) 2-Chloro-4-[(6a-methyl-5,6,6a,7,8,9-hexahydro-4H-2-phenalenyl)carboxamido]benzoic acid

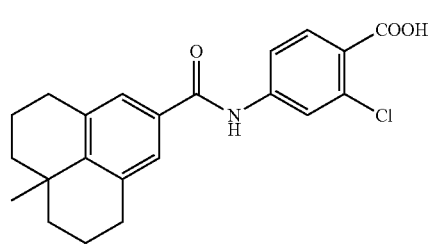

[Formula 43]

A suspension of methyl 2-chloro-4-[(6a-methyl-5,6,6a,7,8,9-hexahydro-4H-2-phenalenyl)carboxamido]benzoate (0.244 g) in ethanol (10 ml) was added with 2 N aqueous sodium hydroxide (2 ml), and the mixture was stirred at room temperature for 2 hours and at 60° C. for 1 hour. The reaction mixture was left to cool and then made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.192 g, yield: 82%) as colorless prisms (melting point: 244-246° C.).

$^1$H-NMR (400 MHz, CD$_3$OD): δ 1.19 (3H, s), 1.52 (2H, td, J=12.9, 5.1 Hz), 1.73 (2H, dt, J=12.9, 4.1 Hz), 1.79-1.90 (2H, m), 2.03-2.20 (2H, m), 2.85 (2H, dt, J=17.1, 8.6 Hz), 3.00 (2H, ddd, J=17.3, 7.7, 3.3 Hz), 7.44 (2H, s), 7.71 (1H, dd, J=8.7, 1.8 Hz), 7.90 (1H, d, J=8.7 Hz), 8.02 (1H, d, J=1.8 Hz)

$^1$H-NMR (400 MHz, DMSO-d$_6$): δ 1.13 (3H, s), 1.45 (2H, td, J=12.9, 5.1 Hz), 1.68 (2H, dt, J=12.9, 3.9 Hz), 1.75-1.83 (2H, m), 1.95-2.10 (2H, m), 2.81 (2H, dt, J=17.3, 8.7 Hz), 2.96 (2H, ddd, J=17.1, 7.6, 3.0 Hz), 7.46 (2H, s), 7.81 (1H, dd, J=8.7, 1.8 Hz), 7.87 (1H, d, J=8.7 Hz), 8.04 (1H, d, J=1.8 Hz), 10.43 (1H, s)

Example 18

(1) Methyl 2-hydroxy-4-[(6a-methyl-5,6,6a,7,8,9-hexahydro-4H-2-phenalenyl)carboxamido]benzoate

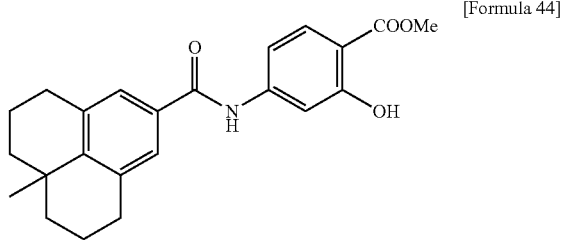

[Formula 44]

A suspension of 6a-methyl-5,6,6a,7,8,9-hexahydro-4H-2-phenalenecarboxylic acid (0.150 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (5 ml), the solution was added with methyl 2-hydroxy-4-aminobenzoate (0.120 g) and 4-dimethylaminopyridine (one pellet), and the mixture was stirred overnight at room temperature. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: ethyl acetate: n-hexane=1:15) to obtain the title compound (0.240 g, yield: 97%). The compound was recrystallized from chloroform-n-hexane to obtain colorless needles (melting point: 179-181° C.).

$^1$H-NMR (400 MHz, CDCl$_3$): δ 1.16 (3H, s), 1.51 (2H, td, J=12.9, 4.8 Hz), 1.71 (2H, dt, J=12.9, 3.9 Hz), 1.78-1.89 (2H, m), 1.99-2.15 (2H, m), 2.83 (2H, dt, J=17.1, 8.6 Hz), 2.97 (2H, ddd, J=17.7, 7.8, 3.3 Hz), 3.94 (3H, s), 7.24 (1H, dd, J=8.7, 2.1 Hz), 7.32 (1H, d, J=2.1 Hz), 7.35 (2H, s), 7.81 (1H, d, J=8.7 Hz), 7.88 (1H, br-s), 10.87 (1H, s)

(2) 2-Hydroxy-4-[(6a-methyl-5,6,6a,7,8,9-hexahydro-4H-2-phenalenyl)carboxamido]benzoic acid

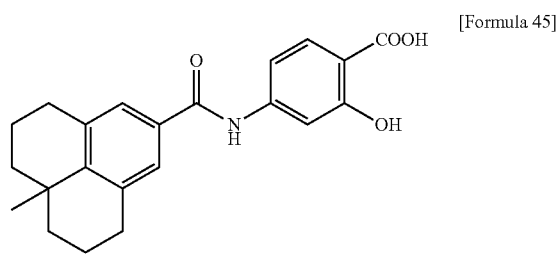

[Formula 45]

A suspension of methyl 2-hydroxy-4-[(6a-methyl-5,6,6a,7,8,9-hexahydro-4H-2-phenalenyl)carboxamido]benzoate (0.234 g) in ethanol (10 ml) was added with 2 N aqueous sodium hydroxide (2 ml), and the mixture was stirred at room temperature for 2 hours and at 60° C. overnight. The reaction mixture was left to cool and then made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.203 g, yield: 90%) as colorless prisms (melting point: 244-245° C.).

$^1$H-NMR (400 MHz, CD$_3$OD): δ 1.19 (3H, s), 1.52 (2H, td, J=12.9, 5.1 Hz), 1.73 (2H, dt, J=12.9, 4.1 Hz), 1.79-1.90 (2H, m), 2.04-2.20 (2H, m), 2.86 (2H, dt, J=17.1, 8.6 Hz), 3.00 (2H, ddd, J=17.4, 7.9, 2.9 Hz), 7.21 (1H, dd, J=8.7, 1.8 Hz), 7.43 (2H, s), 7.46 (1H, d, J=1.8 Hz), 7.81 (1H, d, J=8.7 Hz)

$^1$H-NMR (400 MHz, DMSO-d$_6$): δ 1.13 (3H, s), 1.45 (2H, td, J=12.9, 5.1 Hz), 1.68 (2H, dt, J=12.9, 3.9 Hz), 1.74-1.84 (2H, m), 1.95-2.11 (2H, m), 2.81 (2H, dt, J=17.3, 8.4 Hz), 2.96 (2H, ddd, J=17.4, 7.8, 3.0 Hz), 7.31 (1H, dd, J=8.7, 1.8 Hz), 7.43 (2H, s), 7.51 (1H, d, J=1.8 Hz), 7.74 (1H, d, J=8.7 Hz), 10.29 (1H, s)

Example 19

(1) Methyl 2-methoxy-4-[(6a-methyl-5,6,6a,7,8,9-hexahydro-4H-2-phenalenyl)carboxamido]benzoate

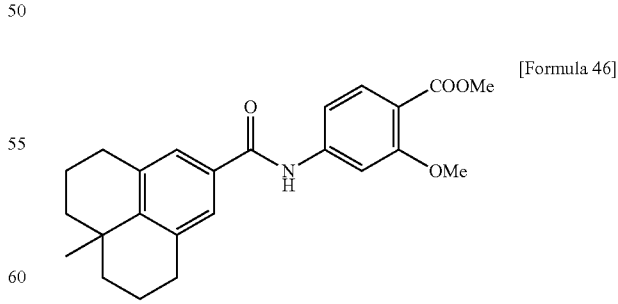

[Formula 46]

A suspension of 6a-methyl-5,6,6a,7,8,9-hexahydro-4H-2-phenalenecarboxylic acid (0.100 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (5 ml), the solution was added with methyl 2-methoxy-4-aminobenzoate (0.087 g) and 4-dimethylaminopyridine (one pellet), and the mixture was stirred overnight at room temperature. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: ethyl acetate:n-hexane=1:5) to obtain the title compound (0.145 g, yield: 85%).

$^1$H-NMR (400 MHz, CDCl$_3$): δ 1.17 (3H, s), 1.51 (2H, td, J=12.9, 5.1 Hz), 1.71 (2H, dt, J=12.9, 3.9 Hz), 1.78-1.89 (2H, m), 1.99-2.15 (2H, m), 2.82 (2H, dt, J=17.1, 8.6 Hz), 2.96 (2H, ddd, J=17.1, 7.8, 3.0 Hz), 3.87 (3H, s), 3.93 (3H, s), 6.97 (1H, dd, J=8.4, 1.8 Hz), 7.38 (2H, s), 7.82 (1H, d, J=1.8 Hz), 7.85 (1H, d, J=8.4 Hz), 8.05 (1H, br-s)

(2) 2-Methoxy-4-[(6a-methyl-5,6,6a,7,8,9-hexahydro-4H-2-phenalenyl)carboxamido]benzoic acid

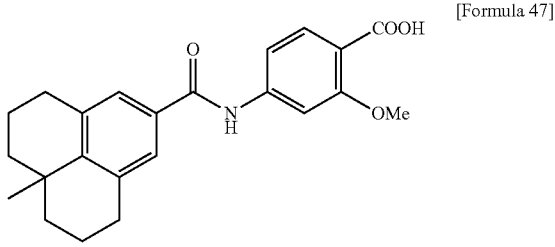

[Formula 47]

A suspension of methyl 2-methoxy-4-[(6a-methyl-5,6,6a,7,8,9-hexahydro-4H-2-phenalenyl)carboxamido]benzoate (0.143 g) in ethanol (10 ml) was added with 2 N aqueous sodium hydroxide (2 ml), and the mixture was stirred at room temperature for 2 hours and at 60° C. for 2 hours. The reaction mixture was left to cool and then made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.110 g, yield: 80%) as colorless needles (melting point: 184-186° C.).

$^1$H-NMR (400 MHz, CD$_3$OD): δ 1.23 (3H, s), 1.53 (2H, td, J=12.9, 4.9 Hz), 1.74 (2H, dt, J=13.1, 4.0 Hz), 1.80-1.91 (2H, m), 2.05-2.21 (2H, m), 2.87 (2H, dt, J=17.1, 8.6 Hz), 3.01 (2H, ddd, J=17.4, 7.9, 3.5 Hz), 3.94 (3H, s), 7.34 (1H, dd, J=8.7, 2.1 Hz), 7.46 (2H, s), 7.73 (1H, d, J=2.1 Hz), 7.84 (1H, d, J=8.7 Hz)

$^1$H-NMR (400 MHz, DMSO-d$_6$): δ 1.14 (3H, s), 1.46 (2H, td, J=12.9, 5.4 Hz), 1.69 (2H, dt, J=12.5, 3.8 Hz), 1.75-1.85 (2H, m), 1.95-2.01 (2H, m), 2.82 (2H, dt, J=17.4, 8.7 Hz), 2.96 (2H, ddd, J=17.3, 7.7, 3.3 Hz), 3.77 (3H, s), 7.41 (1H, dd, J=8.6, 2.1 Hz), 7.46 (2H, s), 7.55-57 (2H, m), 10.19 (1H, s)

Example 20

(1) Methyl 6-[(6a-methyl-5,6,6a,7,8,9-hexahydro-4H-2-phenalenyl)carbamoyl]nicotinate

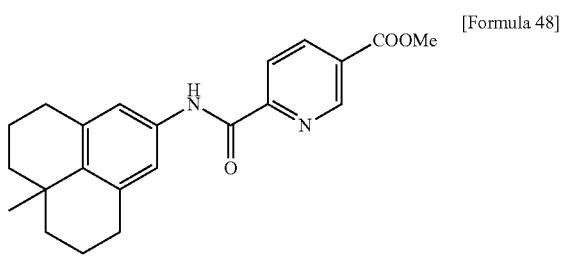

[Formula 48]

A suspension of pyridine-2,5-dicarboxylic acid 5-methyl ester (0.118 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (2 ml), the solution was added with a solution of 6a-methyl-5,6,6a,7,8,9-hexahydro-4H-2-phenalenylamine (0.125 g) in anhydrous benzene (2 ml), and the mixture was stirred at room temperature for 2 hours. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and then dried over anhydrous sodium sulfate. The organic layer was concentrated under reduced pressure, and the resulting residue was purified by silica gel column chromatography (developing solvent: ethyl acetate:n-hexane=1:20) to obtain the title compound (0.180 g, yield: 80%). The compound was recrystallized from chloroform-n-hexane to obtain pale yellow needles (melting point: 141.5-142.5° C.).

$^1$H-NMR (400 MHz, CDCl$_3$): δ 1.17 (3H, s), 1.51 (2H, td, J=12.9, 4.8 Hz), 1.68 (2H, dt, J=12.9, 4.1 Hz), 1.76-1.88 (2H, m), 1.99-2.15 (2H, m), 2.82 (2H, dt, J=17.3, 8.7 Hz), 2.95 (2H, ddd, J=17.4, 8.1, 3.3 Hz), 4.00 (3H, s), 7.33 (2H, s), 8.35 (1H, d, J=8.1 Hz), 8.49 (1H, dd, J=8.1, 2.1 Hz), 9.18 (1H, d, J=2.1 Hz), 9.83 (1H, br-s)

(2) 6-[(6a-Methyl-5,6,6a,7,8,9-hexahydro-4H-2-phenalenyl)carbamoyl]nicotinic acid

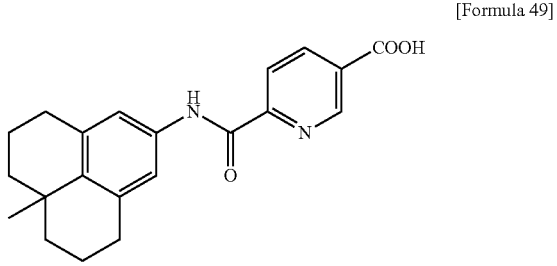

[Formula 49]

A suspension of methyl 6-[(6a-methyl-5,6,6a,7,8,9-hexahydro-4H-2-phenalenyl)carbamoyl]nicotinate (0.176 g) in ethanol (10 ml) was added with 2 N aqueous sodium hydroxide (2 ml), and the mixture was stirred at room temperature for 3 hours. The reaction mixture was made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.153 g, yield: 91%) as pale yellow needles (melting point: 212-213° C.).

$^1$H-NMR (400 MHz, CDCl$_3$): δ 1.17 (3H, s), 1.51 (2H, td, J=12.9, 5.1 Hz), 1.69 (2H, dt, J=12.9, 3.9 Hz), 1.77-1.88 (2H, m), 2.00-2.16 (2H, m), 2.83 (2H, dt, J=17.4, 8.7 Hz), 2.96 (2H, ddd, J=17.3, 8.1, 3.2 Hz), 7.31 (2H, s), 8.42 (1H, d, J=8.1 Hz), 8.57 (1H, dd, J=8.1, 1.8 Hz), 9.26 (1H, d, J=1.8 Hz), 9.87 (1H, s)

Example 21

(1) Methyl 6-[(6a-methyl-5,6,6a,7,8,9-hexahydro-4H-2-phenalenyl)carboxamido]nicotinate

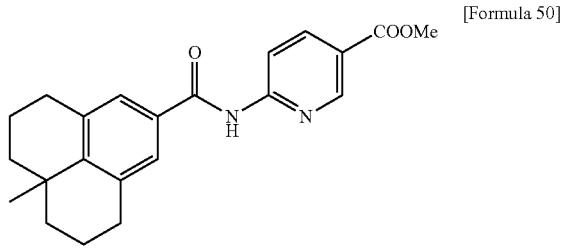

[Formula 50]

A suspension of 6a-methyl-5,6,6a,7,8,9-hexahydro-4H-2-phenalenecarboxylic acid (0.150 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (5 ml), the solution was added with methyl 6-amino-nicotinate (0.109 g) and 4-dimethylaminopyridine (one pellet), and the mixture was stirred overnight. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and dried over anhydrous sodium sulfate. The organic layer was concentrated under reduced pressure, and the resulting residue was purified by silica gel column chromatography (developing solvent: ethyl acetate:n-hexane=1:15) to obtain the title compound (0.194 g, yield: 82%). The compound was recrystallized from chloroform-n-hexane to obtain colorless needles (melting point: 140-141° C.).

$^1$H-NMR (400 MHz, CDCl$_3$): δ 1.18 (3H, s), 1.52 (2H, td, J=13.1, 5.1 Hz), 1.71 (2H, dt, J=12.9, 4.1 Hz), 1.79-1.90 (2H, m), 2.00-2.17 (2H, m), 2.84 (2H, dt, J=17.1, 8.6 Hz), 2.98 (2H, ddd, J=17.4, 7.8, 3.3 Hz), 3.94 (3H, s), 7.44 (2H, s), 8.34 (1H, dd, J=8.7, 2.1 Hz), 8.47 (1H, d, J=8.7 Hz), 8.73 (1H, br-s), 8.92 (1H, d, J=2.1 Hz)

(2) 6-[(6a-Methyl-5,6,6a,7,8,9-hexahydro-4H-2-phenalenyl)carboxamido]nicotinic acid

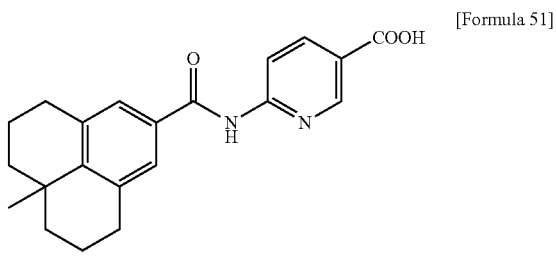

[Formula 51]

A suspension of methyl 6-[(6a-methyl-5,6,6a,7,8,9-hexahydro-4H-2-phenalenyl)carboxamido]nicotinate (0.190 g) in ethanol (10 ml) was added with 2 N aqueous sodium hydroxide (2 ml), and the mixture was stirred at room temperature for 3 hours. The reaction mixture was made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethanol-chloroform to obtain the title compound (0.183 g, yield: 84%) as colorless powdery crystals (melting point: >300° C.).

$^1$H-NMR (400 MHz, DMSO-d$_6$): δ 1.14 (3H, s), 1.48 (2H, td, J=12.9, 5.1 Hz), 1.68 (2H, dt, J=12.9, 4.4 Hz), 1.75-1.84 (2H, m), 1.94-2.11 (2H, m), 2.80 (2H, dt, J=17.3, 8.6 Hz), 2.95 (2H, ddd, J=17.4, 7.7, 3.2 Hz), 7.57 (2H, s), 8.29-8.32 (2H, m), 8.87 (1H, s), 10.88 (1H, s)

Example 22

(1) Methyl 5-[(6a-methyl-5,6,6a,7,8,9-hexahydro-4H-phenalenyl)carbamoyl]pyridine-2-carboxylate

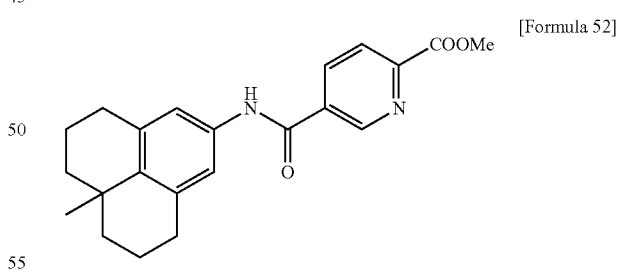

[Formula 52]

A suspension of pyridine-2,5-dicarboxylic acid 2-methyl ester (0.095 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (2 ml), the solution was added with a solution of 6a-methyl-5,6,6a,7,8,9-hexahydro-4H-2-phenalenylamine (0.100 g) in anhydrous benzene (2 ml), and the mixture was stirred at room temperature for 3 hours. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and then dried over anhydrous sodium sulfate. The organic layer was concentrated under reduced pressure, and the resulting residue was purified by silica gel column chromatography (developing solvent: ethyl acetate:n-hexane=1:2) to obtain the title compound (0.162 g, yield: 90%). The compound was recrystallized from chloroform-n-hexane to obtain pale yellow needles (melting point: 173-175° C.).

¹H-NMR (400 MHz, CDCl₃): δ 1.14 (3H, s), 1.47 (2H, td, J=12.9, 5.1 Hz), 1.66 (2H, dt, J=12.9, 4.2 Hz), 1.73-1.84 (2H, m), 1.96-2.12 (2H, m), 2.73 (2H, dt, J=17.1, 8.4 Hz), 2.86 (2H, ddd, J=17.1, 7.8, 3.3 Hz), 4.02 (3H, s), 7.14 (2H, s), 8.16 (1H, d, J=7.8 Hz), 8.25 (1H, br-s), 8.30 (1H, dd, J=7.8, 2.1 Hz), 9.13 (1H, d, J=2.1 Hz)

(2) 5-[(6a-Methyl-5,6,6a,7,8,9-hexahydro-4H-phenalenyl)carbamoyl]pyridine-2-carboxylic acid

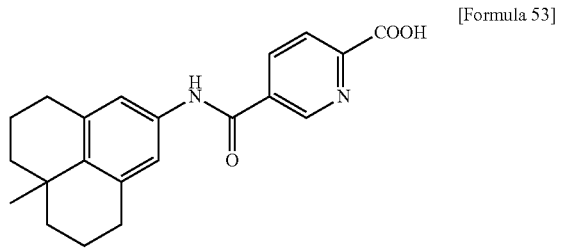

[Formula 53]

A solution of methyl 5-[(6a-methyl-5,6,6a,7,8,9-hexahydro-4H-phenalenyl)carbamoyl]pyridine-2-carboxylate (0.161 g) in ethanol (10 ml) was added with 2 N aqueous sodium hydroxide (1 ml), and the mixture was stirred at room temperature for 3 hours. The reaction mixture was made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethanol-chloroform to obtain the title compound (0.149 g, yield: 96%) as pale yellow powdery crystals (melting point: 199-200° C.).

¹H-NMR (400 MHz, DMSO-d₆): δ 1.09 (3H, s), 1.39 (2H, td, J=12.9, 5.1 Hz), 1.62 (2H, dt, J=12.6, 3.6 Hz), 1.68-1.78 (2H, m), 1.91-2.06 (2H, m), 2.70 (2H, dt, J=17.1, 8.7 Hz), 2.79-2.88 (2H, m), 7.25 (2H, s), 8.13 (1H, d, J=8.1 Hz), 8.40 (1H, dd, J=8.1, 2.1 Hz), 9.12 (1H, d, J=2.1 Hz), 10.30 (1H, s)

Example 23

(1) Methyl 5-[(6a-methyl-5,6,6a,7,8,9-hexahydro-4H-2-phenalenyl)carboxamido]pyridine-2-carboxylate

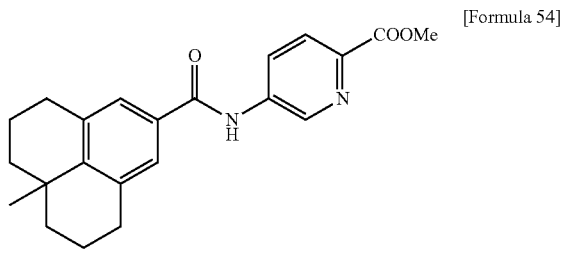

[Formula 54]

A suspension of 6a-methyl-5,6,6a,7,8,9-hexahydro-4H-2-phenalenecarboxylic acid (0.100 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (3 ml) and pyridine (5 ml), the solution was added with methyl 5-amino-pyridine-2-carboxylate (0.065 g) and 4-dimethylaminopyridine (one pellet), and the mixture was stirred overnight. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and dried over anhydrous sodium sulfate. The organic layer was concentrated under reduced pressure, and the resulting residue was purified by silica gel column chromatography (developing solvent: ethyl acetate:n-hexane=1:2) to obtain the title compound (0.090 g, yield: 57%). The compound was recrystallized from chloroform-n-hexane to obtain colorless needles (melting point: 221-222° C.).

¹H-NMR (400 MHz, CDCl₃): δ 1.17 (3H, s), 1.51 (2H, td, J=12.9, 5.1 Hz), 1.68-1.75 (2H, m), 1.79-1.90 (2H, m), 2.00-2.14 (2H, m), 2.84 (2H, dt, J=17.4, 8.4 Hz), 2.97 (2H, ddd, J=17.4, 7.8, 3.3 Hz), 4.00 (3H, s), 7.40 (2H, s), 8.14 (1H, br-s), 8.16 (1H, d, J=8.7 Hz), 8.56 (1H, dd, J=8.7, 2.4 Hz), 8.72 (1H, d, J=2.4 Hz)

(2) 5-[(6a-Methyl-5,6,6a,7,8,9-hexahydro-4H-2-phenalenyl)carboxamido]pyridine-2-carboxylic acid

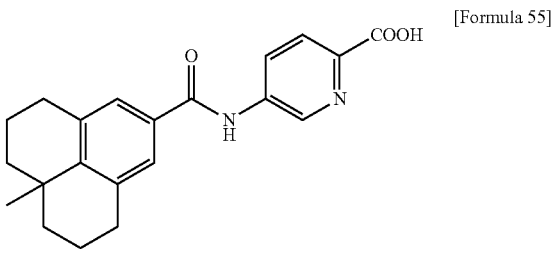

[Formula 55]

A solution of methyl 5-[(6a-methyl-5,6,6a,7,8,9-hexahydro-4H-2-phenalenyl)carboxamido]pyridine-2-carboxylate (0.090 g) in ethanol (10 ml) was added with 2 N aqueous sodium hydroxide (1 ml), and the mixture was stirred at room temperature for 3 hours. The reaction mixture was made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethanol to obtain the title compound (0.082 g, yield: 94%) as colorless needles (melting point: 222-223° C.).

¹H-NMR (400 MHz, DMSO-d₆): δ 1.11 (3H, s), 1.43 (2H, td, J=12.9, 4.8 Hz), 1.66 (2H, dt, J=12.9, 3.6 Hz), 1.71-1.81 (2H, m), 1.93-2.09 (2H, m), 2.80 (2H, dt, J=17.4, 8.7 Hz), 2.94 (2H, ddd, J=17.4, 8.1, 3.3 Hz), 7.47 (2H, s), 8.04 (1H, d, J=8.7 Hz), 8.36 (1H, dd, J=8.7, 2.4 Hz), 9.00 (1H, d, J=2.4 Hz), 10.54 (1H, s)

Example 24

(1) Methyl 5-[(6a-methyl-5,6,6a,7,8,9-hexahydro-4H-2-phenalenyl)carbamoyl]thiophene-2-carboxylate

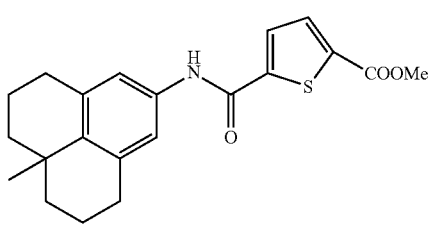

[Formula 56]

A suspension of thiophene-2,5-dicarboxylic acid 2-methyl ester (0.087 g) in anhydrous benzene (3 ml) was added with thionyl chloride (1 ml), and the mixture was refluxed by heating for 3 hours. The organic layer was concentrated under reduced pressure, the resulting residue was dissolved in anhydrous benzene (2 ml) and pyridine (2 ml), the solution was added with a solution of 5,6,6a,7,8,9-hexahydro-4H-2-phenalenylamine (0.090 g) in anhydrous benzene (2 ml), and the mixture was stirred for 3 hours. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and dried over anhydrous sodium sulfate. The organic layer was concentrated under reduced pressure, and the resulting residue was recrystallized from chloroform-n-hexane to obtain the title compound (0.125 g, yield: 76%) as colorless needles (melting point: 211.5-212.5° C.).

$^1$H-NMR (400 MHz, CDCl$_3$): δ 1.15 (3H, s), 1.49 (2H, td, J=12.9, 5.4 Hz), 1.67 (2H, dt, J=12.9, 3.9 Hz), 1.75-1.86 (2H, m), 1.98-2.14 (2H, m), 2.78 (2H, dt, J=17.3, 8.7 Hz), 2.91 (2H, ddd, J=17.3, 7.8, 3.3 Hz), 3.92 (3H, s), 7.13 (2H, s), 7.52 (1H, d, J=3.9 Hz), 7.56 (1H, br-s), 7.76 (1H, d, J=3.9 Hz)

(2) 5-[(6a-Methyl-5,6,6a,7,8,9-hexahydro-4H-2-phenalenyl)carbamoyl]thiophene-2-carboxylic acid

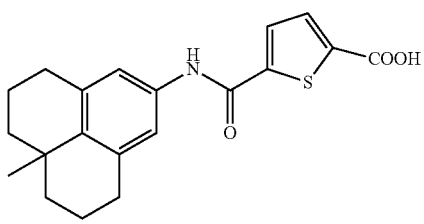

[Formula 57]

A solution of methyl 5-[(6a-methyl-5,6,6a,7,8,9-hexahydro-4H-2-phenalenyl)carbamoyl]thiophene-2-carboxylate (0.123 g) in ethanol (10 ml) was added with 2 N aqueous sodium hydroxide (1 ml), and the mixture was stirred at room temperature for 3 hours. The reaction mixture was made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethanol to obtain the title compound (0.107 g, yield: 91%) as pale yellow powdery crystals (melting point: 271-272° C.).

$^1$H-NMR (400 MHz, DMSO-d$_6$): δ 1.08 (3H, s), 1.38 (2H, td, J=12.9, 5.1 Hz), 1.61 (2H, dt, J=12.6, 3.9 Hz), 1.68-1.79 (2H, m), 1.88-2.04 (2H, m), 2.68 (2H, dt, J=17.4, 8.7 Hz), 2.82 (2H, ddd, J=17.7, 8.1, 3.3 Hz), 7.20 (2H, s), 7.72 (1H, d, J=3.9 Hz), 7.94 (1H, d, J=3.9 Hz), 10.16 (1H, s)

Example 25

(1) Methyl 5-[(6a-methyl-5,6,6a,7,8,9-hexahydro-4H-2-phenalenyl)carboxamido]thiophene-2-carboxylate

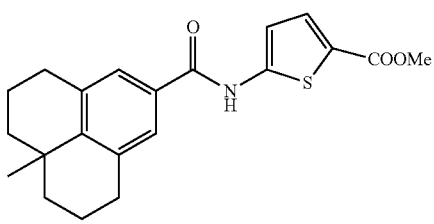

[Formula 58]

A suspension of 6a-methyl-5,6,6a,7,8,9-hexahydro-4H-2-phenalenecarboxylic acid (0.110 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (2 ml), the solution was added with methyl 5-amino-thiophene-2-carboxylate (0.079 g) and 4-dimethylaminopyridine (one pellet), and the mixture was stirred overnight. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and dried over anhydrous sodium sulfate. The organic layer was concentrated under reduced pressure, and the resulting residue was purified by silica gel column chromatography (developing solvent: ethyl acetate:n-hexane=1:15) to obtain the title compound (0.109 g, yield: 62%). The compound was recrystallized from chloroform-n-hexane to obtain colorless needles (melting point: 179-180° C.).

$^1$H-NMR (400 MHz, CDCl$_3$): δ 1.15 (3H, s), 1.49 (2H, td, J=12.9, 5.1 Hz), 1.69 (2H, dt, J=12.9, 3.9 Hz), 1.76-1.87 (2H, m), 1.97-2.12 (2H, m), 2.73-2.84 (2H, m), 2.88-2.96 (2H, m), 3.86 (3H, s), 6.76 (1H, d, J=4.2 Hz), 7.39 (2H, s), 7.63 (1H, d, J=4.2 Hz), 9.09 (1H, br-s)

(2) 5-[(6a-Methyl-5,6,6a,7,8,9-hexahydro-4H-2-phenalenyl)carboxamido]thiophene-2-carboxylic acid

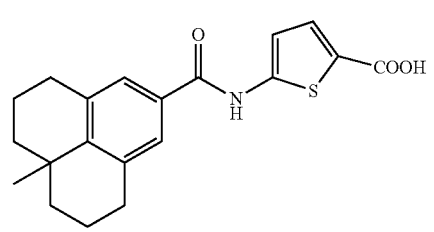

[Formula 59]

A suspension of methyl 5-[(6a-methyl-5,6,6a,7,8,9-hexahydro-4H-2-phenalenyl)carboxamido]thiophene-2-carboxylate (0.075 g) in ethanol (5 ml) was added with 2 N aqueous sodium hydroxide (1 ml), and the mixture was stirred at 60° C. for 2 hours. The reaction mixture was left to cool and then made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.051 g, yield: 71%) as colorless powdery crystals (melting point: 259-260° C.).

$^1$H-NMR (400 MHz, DMSO-d$_6$): δ 1.11 (3H, s), 1.42 (2H, td, J=12.9, 4.5 Hz), 1.62-1.69 (2H, m), 1.72-1.80 (2H, m), 1.92-2.08 (2H, m), 2.79 (2H, dt, J=17.3, 8.7 Hz), 2.94 (2H, ddd, J=17.7, 8.1, 3.3 Hz), 6.91 (1H, d, J=4.2 Hz), 7.48 (2H, s), 7.61 (1H, d, J=4.2 Hz), 11.80 (1H, s)

Example 26

4-[(6a-Methyl-5,6,6a,7,8,9-hexahydro-4H-2-phenalenyl)sulfamoyl]benzoic acid

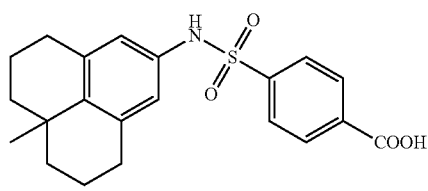

[Formula 60]

6a-Methyl-5,6,6a,7,8,9-hexahydro-4H-2-phenalenylamine (0.100 g) was dissolved in pyridine (5 ml) and anhydrous benzene (2 ml), the solution was added with 4-chlorosulfonylbenzoic acid (0.115 g) and 4-dimethylaminopyridine (one pellet), and the mixture was stirred overnight at room temperature. The reaction mixture was added with 2 N aqueous hydrochloric acid and thereby made acidic, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.110 g, yield: 57%) as colorless needles (melting point: 215-217° C.).

$^1$H-NMR (400 MHz, DMSO-d$_3$): δ 0.99 (3H, s), 1.29 (2H, td, J=12.9, 4.5 Hz), 1.50-1.57 (2H, m), 1.61-4.69 (2H, m), 1.81-1.95 (2H, m), 2.50-2.61 (1H, m), 2.64-2.74 (4H, m), 6.56 (2H, s), 7.85 (2H, d, J=8.1 Hz), 8.05 (2H, d, J=8.1 Hz), 10.14 (1H, s)

Example 27

(1) Ethyl (6,7,8,9-tetrahydro-5-benzocycloheptenylidene)acetate

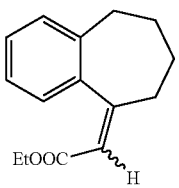

[Formula 61]

A suspension of sodium hydride (60%, 2.25 g) in anhydrous benzene (100 ml) was slowly added with a solution of diethyl phosphonoacetate (14.0 g) in anhydrous benzene (20 ml) at 0° C., and the mixture was stirred at 0° C. for 15 minutes. The mixture was added with a solution of 1-benzosuberone (5.00 g) in anhydrous benzene (30 ml), and the mixture was stirred at 0° C. for 15 minutes, and then refluxed overnight by heating. The reaction mixture was left to cool and then added with saturated aqueous ammonium chloride, and the mixture was extracted with ethyl acetate. The organic layer was washed successively with water and saturated brine, and dried over anhydrous sodium sulfate. The organic layer was concentrated under reduced pressure, and the resulting residue was purified by silica gel column chromatography (developing solvent: ethyl acetate:n-hexane=1:200) to quantitatively obtain the title compound.

(2) Ethyl (6,7,8,9-tetrahydro-5H-5-benzocycloheptenyl)acetate

[Formula 62]

A solution of ethyl (6,7,8,9-tetrahydro-5-benzocycloheptenylidene)acetate (0.550 g) in ethyl acetate (10 ml) was added with 10% palladium/carbon (0.055 g), and the mixture was stirred for 3 hours under a hydrogen flow. The reaction mixture was filtered through Celite, and then the solvent of the filtrate was concentrated under reduced pressure to obtain the title compound (0.551 g, yield: 99%).

$^1$H-NMR (400 MHz, CDCl$_3$): δ 1.22 (3H, t, J=7.2 Hz), 1.47-1.64 (2H, m), 1.72-1.95 (4H, m), 2.65-2.79 (2H, m), 2.82-2.95 (2H, m), 3.43-3.52 (1H, m), 4.12 (2H, q, J=7.2 Hz), 7.07-7.15 (4H, m)

(3) (6,7,8,9-Tetrahydro-5H-5-benzocycloheptenyl)acetaldehyde

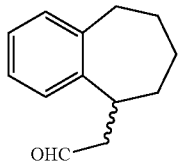

[Formula 63]

Ethyl (6,7,8,9-tetrahydro-5H-5-benzocycloheptenyl)acetate (0.550 g) was dissolved in anhydrous toluene (10 ml), and the solution was slowly added with diisobutylaluminum hydride (0.93 M n-hexane solution, 2.8 ml) at −78° C. under an argon flow. The reaction mixture was stirred −78° C. for 1 hour, and then slowly added with methanol (3 ml) and 2 N aqueous hydrochloric acid, and the mixture was extracted with ethyl acetate. The organic layer was washed successively with water and saturated brine, and dried over anhydrous sodium sulfate. The organic layer was concentrated under reduced pressure, and the resulting residue was purified by silica gel column chromatography (developing solvent: ethyl acetate:n-hexane=1:300) to obtain the title compound (0.432 g, yield: 97%).

$^1$H-NMR (400 MHz, CDCl$_3$): δ 1.48-1.65 (2H, m), 1.73-1.90 (4H, m), 2.75-2.98 (4H, m), 3.53-3.61 (1H, m), 7.05-7.16 (4H, m), 9.80 (1H, t, J=2.1 Hz)

(4) Ethyl 4-(6,7,8,9-tetrahydro-5H-5-benzocycloheptenyl)-2-butenoate

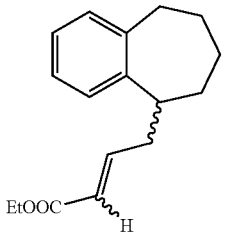

[Formula 64]

A suspension of sodium hydride (60%, 0.130 g) in anhydrous benzene (5 ml) was slowly added with diethyl phosphonoacetate (0.750 g) at 0° C., and the mixture was stirred at 0° C. for 10 minutes. The mixture was added with a solution of (6,7,8,9-tetrahydro-5H-5-benzocycloheptenyl)acetaldehyde (0.419 g) in anhydrous benzene (5 ml), and the mixture was stirred at 0° C. for 5 minutes, and then refluxed overnight by heating. The reaction mixture was left to cool and then added with saturated aqueous ammonium chloride, and the mixture was extracted with ethyl acetate. The organic layer was washed successively with water and saturated brine, and dried over anhydrous sodium sulfate. The organic layer was concentrated under reduced pressure, and the resulting residue was purified by silica gel column chromatography (developing solvent: ethyl acetate:n-hexane=1:300) to obtain the title compound (0.544 g, yield: 94%).

(5) Ethyl 4-(6,7,8,9-tetrahydro-5H-5-benzocycloheptenyl)butyrate

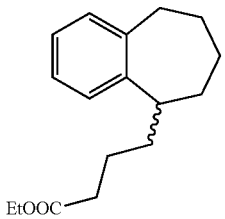

[Formula 65]

A solution of ethyl 4-(6,7,8,9-tetrahydro-5H-5-benzocycloheptenyl)-2-butenoate (0.544 g) in ethyl acetate (10 ml) was added with 10% palladium/carbon (0.054 g), and the mixture was stirred for 3 hours under a hydrogen flow. The reaction mixture was filtered through Celite, and then the solvent of the filtrate was concentrated under reduced pressure to obtain the title compound (0.534 g, yield: 97%).

$^1$H-NMR (400 MHz, CDCl$_3$): δ 1.25 (3H, t, J=7.2 Hz), 1.58-1.89 (10H, m), 2.32 (2H, t, J=7.2 Hz), 2.83 (3H, dd, J=11.4, 4.8 Hz), 4.12 (2H, q, J=7.2 Hz), 7.06-7.09 (2H, m), 7.10-7.12 (2H, m)

(6) 4-(6,7,8,9-Tetrahydro-5H-5-benzocycloheptenyl)butyric acid

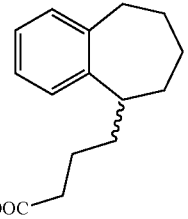

[Formula 66]

A solution of ethyl 4-(6,7,8,9-tetrahydro-5H-5-benzocycloheptenyl)butyrate (0.534 g) in methanol (10 ml) was added with 2 N aqueous sodium hydroxide (2 ml), and the mixture was stirred at room temperature for 3 hours. The reaction mixture was added with 2 N aqueous hydrochloric acid and thereby made acidic, and the mixture was extracted with chloroform. The organic layer was washed successively with water and saturated brine, dried over anhydrous sodium sulfate, and then concentrated under reduced pressure to quantitatively obtain the title compound.

$^1$H-NMR (400 MHz, CDCl$_3$): δ 1.51-1.92 (10H, m), 2.38 (2H, t, J=7.2 Hz), 2.80-2.85 (3H, m), 7.07-7.12 (4H, m)

(7) 5,6,7,7a,8,9,10,11-Octahydro-4-benzo[ef]heptalenone

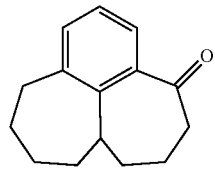

[Formula 67]

4-(6,7,8,9-Tetrahydro-5H-5-benzocycloheptenyl)butyric acid (0.478 g) was added with polyphosphoric acid (4.80 g), and the mixture was stirred at 110° C. for 4 hours. The reaction mixture was poured into ice water, and the mixture was extracted with ethyl acetate. The organic layer was washed successively with water and saturated brine, and dried over anhydrous sodium sulfate. The organic layer was concentrated under reduced pressure, and the resulting residue was purified by silica gel column chromatography (developing solvent: ethyl acetate:n-hexane=1:100) to obtain the title compound (0.326 g, yield: 74%).

$^1$H-NMR (400 MHz, CDCl$_3$): δ 1.45-1.54 (1H, m), 1.61-1.75 (2H, m), 1.92-1.99 (7H, m), 2.56-2.62 (1H, m), 2.81-2.97 (3H, m), 3.40-3.48 (1H, m), 7.13 (1H, t, J=7.5 Hz), 7.20 (1H, dd, J=7.5, 1.5 Hz), 7.37 (1H, dd, J=7.5, 1.5 Hz)

(8) 5,6,7,7a,8,9,10,11-Octahydro-4H-benzo[ef]heptalene

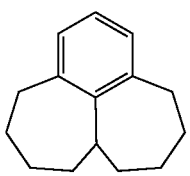

[Formula 68]

A solution of 5,6,7,7a,8,9,10,11-octahydro-4-benzo[ef]heptalenone (0.280 g) in trifluoroacetic acid (2 ml) was added with triethylsilane (0.42 ml), and the mixture was stirred overnight at 60° C. The reaction mixture was concentrated under reduced pressure, the resulting residue was poured into ice water, and the mixture was extracted with ethyl acetate. The organic layer was washed successively with saturated aqueous sodium hydrogencarbonate, water and saturated brine, and dried over anhydrous sodium sulfate. The organic layer was concentrated under reduced pressure, and the resulting residue was purified by silica gel column chromatography (developing solvent: n-hexane) to obtain the title compound (0.195 g, yield: 74%).

$^1$H-NMR (400 MHz, CDCl$_3$): δ 1.47-1.66 (6H, m), 1.78-1.96 (6H, m), 2.81-2.86 (4H, m), 3.20-3.29 (1H, m), 6.90-6.99 (3H, m)

(9) 1-(5,6,7,7a,8,9,10,11-Octahydro-4H-2-benzo[ef]heptalenyl)ethanone

[Formula 69]

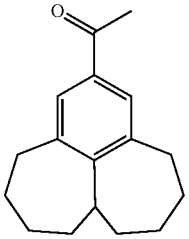

A suspension of aluminum chloride (0.155 g) in carbon disulfide (3 ml) was added with acetyl chloride (0.090 ml), and the mixture was stirred at room temperature for 15 minutes. The reaction mixture was cooled to 0° C., and slowly added with 5,6,7,7a,8,9,10,11-octahydro-4H-benzo[ef]heptalene (0.194 g) dissolved in carbon disulfide (2 ml), and the mixture was stirred at 0° C. for 30 minutes and at room temperature overnight. The reaction mixture was poured into ice water, the mixture was extracted with ethyl acetate, and the organic layer was washed successively with water and saturated brine, and dried over anhydrous sodium sulfate. The organic layer was concentrated under reduced pressure, and the resulting residue was purified by silica gel column chromatography (developing solvent: ethyl acetate:n-hexane=1: 300) to obtain 1-(5,6,7,7a,8,9,10,11-octahydro-4H-1-benzo[ef]heptalenyl)ethanone (0.042 g, yield: 18%) and the title compound (0.180 g, yield: 77%).

$^1$H-NMR (400 MHz, CDCl$_3$): δ 1.47-1.70 (6H, m), 1.78-1.98 (6H, m), 2.56 (3H, s), 2.90 (4H, t, J=5.4 Hz), 3.24-3.31 (1H, m), 7.52 (2H, s)

(10) 5,6,7,7a,8,9,10,11-Octahydro-4H-2-benzo[ef]heptalenecarboxylic acid

[Formula 70]

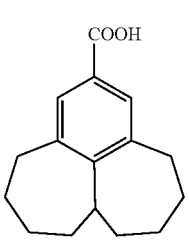

2.5 N Aqueous sodium hydroxide (4 ml) was cooled to 0° C., and slowly added with bromine (0.13 ml), and then the mixture was diluted with 1,4-dioxane (3 ml) to obtain a yellow solution. A solution of 1-(5,6,7,7a,8,9,10,11-octahydro-4H-2-benzo[ef]heptalenyl)ethanone (0.180 g) in water (2 ml) and 1,4-dioxane (5 ml) was cooled to 0° C., and slowly added with the yellow solution prepared above, and the mixture was stirred at 0° C. for 30 minutes and at room temperature for 3 hours. The reaction mixture was cooled to 0° C., added with 10% aqueous sodium sulfite, and then made acidic with 2 N aqueous hydrochloric acid, and the mixture was extracted with chloroform. The organic layer was washed successively with water and saturated brine, and dried over anhydrous sodium sulfate. The organic layer was concentrated under reduced pressure, and the resulting residue was recrystallized from ethyl acetate-n-hexane to obtain the title compound (0.161 g, yield: 88%) as colorless needles (melting point: 178.5-179.5° C.).

$^1$H-NMR (400 MHz, CDCl$_3$): δ 1.48-1.71 (6H, m), 1.78-1.96 (6H, m), 2.91 (4H, t, J=5.4 Hz), 3.26-3.33 (1H, m), 7.67 (2H, s)

(11) 5,6,7,7a,8,9,10,11-Octahydro-4H-2-benzo[ef]heptalenylamine

[Formula 71]

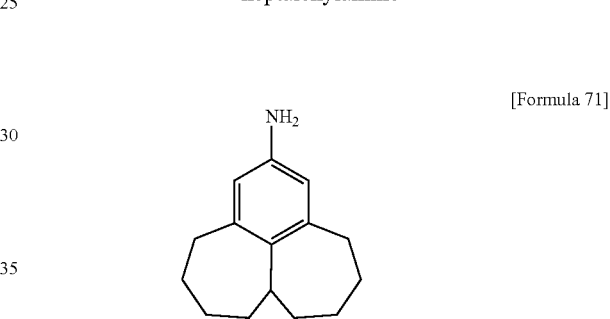

A solution of 5,6,7,7a,8,9,10,11-octahydro-4H-2-benzo[ef]heptalenecarboxylic acid (0.250 g) in anhydrous benzene (2 ml) was added with thionyl chloride (1 ml), and the mixture was refluxed by heating for 3 hours. The mixture was concentrated under reduced pressure, a solution of the resulting residue in anhydrous tetrahydrofuran (10 ml) was cooled to 0° C., and added with a solution of sodium azide (0.199 g) in water (1 ml), and the mixture was stirred at 0° C. for 10 minutes and at room temperature for 1 hour. The reaction mixture was added with saturated aqueous sodium hydrogencarbonate, and the mixture was extracted with diethyl ether. The organic layer was washed successively with water and saturated brine, and dried over anhydrous sodium sulfate. The organic layer was concentrated under reduced pressure, the resulting residue was dissolved in acetic acid (5 ml) and water (2 ml), and the solution was refluxed by heating for 1 hour. The reaction mixture was left to cool, then added with saturated aqueous sodium hydrogencarbonate and thereby made alkaline, and then the mixture was extracted with ethyl acetate. The organic layer was washed successively with water and saturated brine, and dried over anhydrous sodium sulfate. The organic layer was concentrated under reduced pressure, the resulting residue was dissolved in methanol (5 ml), the solution was added with concentrated hydrochloric acid (5 ml), and the mixture was refluxed by heating for 3 hours. The reaction mixture was left to cool and then made alkaline with 2 N aqueous sodium hydroxide, and the mixture was extracted with diethyl ether. The organic layer was washed successively with water and saturated brine, and dried over anhydrous sodium sulfate. The organic layer was concentrated under reduced pressure, and the resulting residue was purified by silica gel column chromatography (developing solvent: ethyl acetate:n-hexane=1:50) to obtain the title compound (0.134 g, yield: 61%).

$^1$H-NMR (400 MHz, CDCl$_3$): δ 1.44-1.64 (6H, m), 1.76-1.92 (6H, m), 2.70-2.76 (4H, m), 3.09-3.16 (1H, m), 3.43 (2H, br-s), 6.31 (2H, s)

(12) Methyl 4-[(5,6,7,7a,8,9,10,11-octahydro-4H-2-benzo[ef]heptalenyl)carbamoyl]benzoate

[Formula 72]

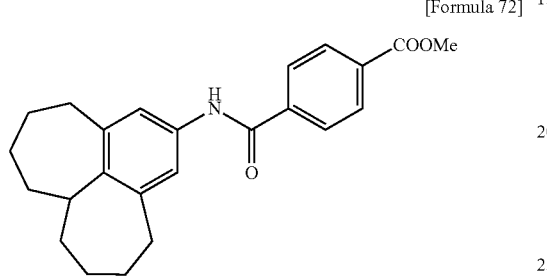

A solution of 5,6,7,7a,8,9,10,11-octahydro-4H-2-benzo[ef]heptalenylamine (0.053 g) in anhydrous benzene (3 ml) and pyridine (1 ml) was added with monomethyl terephthalate chloride (0.064 g), and the mixture was stirred at room temperature for 4 hours. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and then dried over anhydrous sodium sulfate. The organic layer was concentrated under reduced pressure, and the resulting residue was recrystallized from chloroform-n-hexane to obtain the title compound (0.068 g, yield: 73%) as colorless needles (melting point: 199-200° C.).

$^1$H-NMR (400 MHz, CDCl$_3$): δ 1.51-1.69 (6H, m), 1.79-1.95 (6H, m), 2.84 (4H, t, J=5.4 Hz), 3.18-3.25 (1H, m), 3.96 (3H, s), 7.23 (2H, s), 7.69 (1H, br-s), 7.90 (2H, d, J=8.7 Hz), 8.14 (2H, d, J=8.7 Hz)

(13) 4-[(5,6,7,7a,8,9,10,11-Octahydro-4H-2-benzo[ef]heptalenyl)carbamoyl]benzoic acid

[Formula 73]

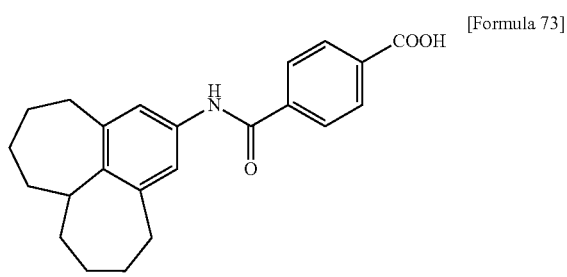

A suspension of methyl 4-[(5,6,7,7a,8,9,10,11-octahydro-4H-2-benzo[ef]heptalenyl)carbamoyl]benzoate (0.066 g) in ethanol (5 ml) was added with 2 N aqueous sodium hydroxide (1 ml), and the mixture was stirred at room temperature for 3 hours. The reaction mixture was made acidic with 2 N aqueous hydrochloric acid, and the mixture was extracted with chloroform. The organic layer was washed with saturated brine, and dried over anhydrous sodium sulfate. The organic layer was concentrated under reduced pressure, and the resulting residue was recrystallized from ethyl acetate-n-hexane to obtain the title compound (0.059 g, yield: 92%) as colorless needles (melting point: 280-281° C.).

$^1$H-NMR (400 MHz, DMSO-d$_6$): δ 1.34-1.59 (6H, m), 1.69-1.88 (6H, m), 2.71-2.80 (4H, m), 3.10-3.21 (1H, m), 7.27 (2H, s), 7.95 (2H, d, J=8.1 Hz), 8.05 (2H, d, J=8.1 Hz), 10.17 (1H, s)

Example 28

(1) Methyl 4-[(5,6,7,7a,8,9,10,11-octahydro-4H-2-benzo[ef]heptalenyl)carboxamido]benzoate

[Formula 74]

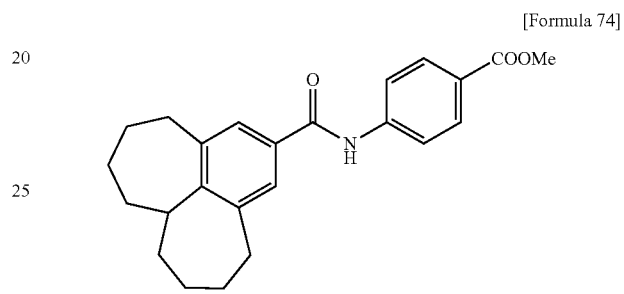

A suspension of 5,6,7,7a,8,9,10,11-octahydro-4H-2-benzo[ef]heptalenecarboxylic acid (0.062 g) in anhydrous benzene (3 ml) was added with thionyl chloride (2 ml), and the mixture was refluxed by heating for 3 hours. The reaction mixture was concentrated under reduced pressure, the resulting residue was dissolved in anhydrous benzene (3 ml) and pyridine (2 ml), the solution was added with methyl 4-aminobenzoate (0.046 g) and 4-dimethylaminopyridine (one pellet), and the mixture was stirred overnight. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: ethyl acetate:n-hexane=1:20) to obtain the title compound (0.064 g, yield: 67%).

$^1$H-NMR (400 MHz, CDCl$_3$): δ 1.51-1.71 (6H, m), 1.79-1.97 (6H, m), 2.92 (4H, t, J=5.4 Hz), 3.26-3.33 (1H, m), 3.91 (3H, s), 7.42 (2H, s), 7.74 (2H, d, J=8.7 Hz), 7.94 (1H, br-s), 8.05 (2H, d, J=8.7 Hz)

(2) 4-[(5,6,7,7a,8,9,10,11-Octahydro-4H-2-benzo[ef]heptalenyl)carboxamido]benzoic acid

[Formula 75]

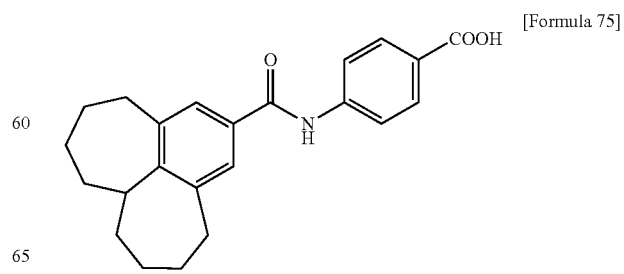

A suspension of methyl 4-[(5,6,7,7a,8,9,10,11-octahydro-4H-2-benzo[ef]heptalenyl)carboxamido]benzoate (0.064 g) in ethanol (5 ml) was added with 2 N aqueous sodium hydroxide (1 ml), and the mixture was stirred at room temperature for 3 hours. The reaction mixture was made acidic with 2 N aqueous hydrochloric acid, and the mixture was extracted with chloroform. The organic layer was washed with saturated brine, dried over anhydrous sodium sulfate, and then concentrated under reduced pressure, and the resulting residue was recrystallized from ethyl acetate-n-hexane to obtain the title compound (0.054 g, yield: 87%) as colorless needles (melting point: 275-276° C.).

$^1$H-NMR (400 MHz, DMSO-$d_6$): δ 1.37-1.60 (6H, s), 1.70-1.90 (6H, m), 2.84-2.87 (4H, m), 3.20-3.31 (1H, m), 7.48 (2H, s), 7.83 (2H, d, J=8.7 Hz), 7.89 (2H, d, J=8.7 Hz), 10.32 (1H, s)

Example 29

2-Fluoro-4-[(5,6,7,7a,8,9,10,11-octahydro-4H-2-benzo[ef]heptalenyl)carboxamido]benzoic acid

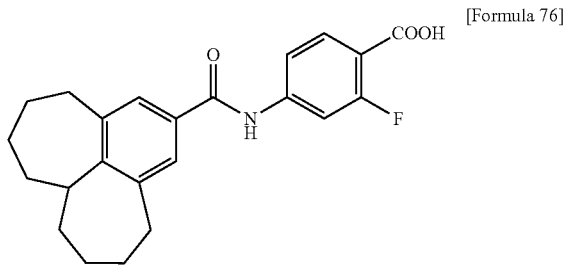

[Formula 76]

A suspension of 5,6,7,7a,8,9,10,11-octahydro-4H-2-benzo[ef]heptalenecarboxylic acid (0.090 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (5 ml), the solution was added with methyl 2-fluoro-4-aminobenzoate (0.075 g) and 4-dimethylaminopyridine (one pellet), and the mixture was stirred overnight. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: ethyl acetate:n-hexane=1:10) to obtain methyl 2-fluoro-4-[(5,6,7,7a,8,9,10,11-octahydro-4H-2-benzo[ef]heptalenyl)carboxamido]benzoate (0.052 g, yield: 36%).

$^1$H-NMR (400 MHz, CDCl$_3$): δ 1.51-1.71 (6H, m), 1.79-1.95 (6H, m), 2.91 (4H, t, J=5.7 Hz), 3.26-3.32 (1H, m), 3.92 (3H, s), 7.31 (1H, dd, J=8.4, 2.1 Hz), 7.41 (2H, s), 7.77 (1H, dd, J=12.9, 2.1 Hz), 7.94 (1H, br-s), 7.95 (1H, t, J=8.4 Hz)

A suspension of the aforementioned ester (0.050 g) in ethanol (5 ml) was added with 2 N aqueous sodium hydroxide (1 ml), and the mixture was stirred at 60° C. for 3 hours. The reaction mixture was made acidic with 2 N aqueous hydrochloric acid, and the mixture was extracted with chloroform. The organic layer was washed with saturated brine, dried over anhydrous sodium sulfate, and then concentrated under reduced pressure, and the resulting residue was recrystallized from ethyl acetate-n-hexane to obtain the title compound (0.031 g, yield: 65%) as colorless needles (melting point: 266-267° C.).

$^1$H-NMR (400 MHz, DMSO-$d_6$): δ 1.43-1.56 (6H, m), 1.74-1.91 (6H, m), 2.88 (4H, t, J=5.7 Hz), 3.11-3.19 (1H, m), 7.50 (2H, s), 7.62 (1H, dd, J=8.7, 2.1 Hz), 7.78-7.89 (2H, m), 10.47 (1H, s)

Example 30

2-Chloro-4-[(5,6,7,7a,8,9,10,11-octahydro-4H-2-benzo[ef]heptalenyl)carboxamido]benzoic acid

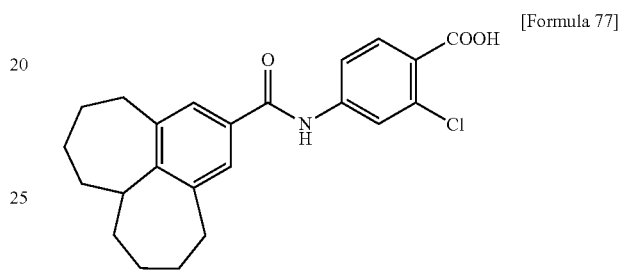

[Formula 77]

A suspension of 5,6,7,7a,8,9,10,11-octahydro-4H-2-benzo[ef]heptalenecarboxylic acid (0.090 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (5 ml), the solution was added with methyl 2-chloro-4-aminobenzoate (0.082 g) and 4-dimethylaminopyridine (one pellet), and the mixture was stirred overnight. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: ethyl acetate:n-hexane=1:10) to obtain methyl 2-chloro-4-[(5,6,7,7a,8,9,10,11-octahydro-4H-2-benzo[ef]heptalenyl)carboxamido]benzoate (0.080 g, yield: 53%).

$^1$H-NMR (400 MHz, CDCl$_3$): δ 1.51-1.71 (6H, m), 1.79-1.98 (6H, m), 2.91 (4H, t, J=5.7 Hz), 3.25-3.32 (1H, m), 3.92 (3H, s), 7.41 (2H, s), 7.65 (1H, dd, J=8.7, 2.1 Hz), 7.84 (1H, d, J=2.1 Hz), 7.91 (1H, d, J=8.7 Hz), 7.93 (1H, br-s)

A suspension of the aforementioned ester (0.075 g) in ethanol (5 ml) was added with 2 N aqueous sodium hydroxide (1 ml), and the mixture was stirred at 60° C. for 3 hours. The reaction mixture was made acidic with 2 N aqueous hydrochloric acid, and the mixture was extracted with chloroform. The organic layer was washed with saturated brine, dried over anhydrous sodium sulfate, and then concentrated under reduced pressure, and the resulting residue was recrystallized from ethyl acetate-n-hexane to obtain the title compound (0.058 g, yield: 81%) as colorless needles (melting point: 243-244° C.).

$^1$H-NMR (400 MHz, DMSO-$d_6$): δ 1.43-1.59 (6H, m), 1.72-1.90 (6H, m), 2.87 (4H, t, J=5.4 Hz), 3.12-3.18 (1H, m), 7.50 (2H, s), 7.79 (1H, dd, J=8.4, 1.8 Hz), 7.84 (1H, d, J=8.4 Hz), 8.02 (1H, d, J=1.8 Hz), 10.38 (1H, s)

Example 31

2-Hydroxy-4-[(5,6,7,7a,8,9,10,11-octahydro-4H-2-benzo[ef]heptalenyl)carboxamido]benzoic acid

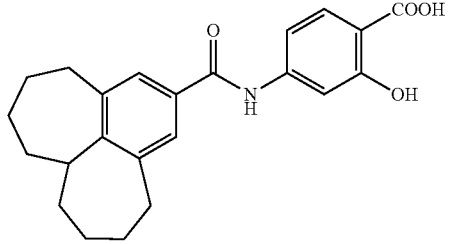

[Formula 78]

A suspension of 5,6,7,7a,8,9,10,11-octahydro-4H-2-benzo[ef]heptalenecarboxylic acid (0.090 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (5 ml), the solution was added with methyl 2-hydroxy-4-aminobenzoate (0.074 g) and 4-dimethylaminopyridine (one pellet), and the mixture was stirred overnight. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: ethyl acetate:n-hexane=1:10) to obtain methyl 2-hydroxy-4-[(5,6,7,7a,8,9,10,11-octahydro-4H-2-benzo[ef]heptalenyl)carboxamido]benzoate (0.041 g, yield: 28%).

$^1$H-NMR (400 MHz, CDCl$_3$): δ 1.48-1.70 (6H, m), 1.78-1.96 (6H, m), 2.90 (4H, t, J=5.7 Hz), 3.24-3.31 (1H, m), 3.94 (3H, s), 7.24 (1H, dd, J=8.7, 2.1 Hz), 7.30 (1H, d, J=2.1 Hz), 7.40 (2H, s), 7.81 (1H, d, J=8.7 Hz), 7.89 (1H, br-s), 10.86 (1H, s)

A suspension of the aforementioned ester (0.040 g) in ethanol (5 ml) was added with 2 N aqueous sodium hydroxide (1 ml), and the mixture was stirred at 60° C. for 3 hours. The reaction mixture was made acidic with 2 N aqueous hydrochloric acid, and the mixture was extracted with chloroform. The organic layer was washed with saturated brine, dried over anhydrous sodium sulfate, and then concentrated under reduced pressure, and the resulting residue was recrystallized from ethyl acetate-n-hexane to obtain the title compound (0.024 g, yield: 62%) as colorless needles (melting point: 242-243° C.).

$^1$H-NMR (400 MHz, DMSO-d$_6$): δ 1.43-1.59 (6H, m), 1.71-1.91 (6H, m), 2.87 (4H, t, J=5.4 Hz), 3.06-3.13 (1H, m), 7.29 (1H, dd, J=8.7, 1.8 Hz), 7.48 (2H, s), 7.49 (1H, d, J=1.8 Hz), 7.72 (1H, d, J=8.7 Hz), 10.25 (1H, s)

Example 32

2-Methoxy-4-[(5,6,7,7a,8,9,10,11-octahydro-4H-2-benzo[ef]heptalenyl)carboxamido]benzoic acid

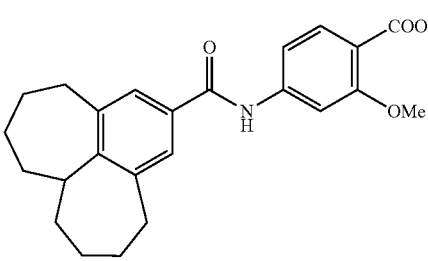

[Formula 79]

A suspension of 5,6,7,7a,8,9,10,11-octahydro-4H-2-benzo[ef]heptalenecarboxylic acid (0.090 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (5 ml), the solution was added with methyl 2-methoxy-4-aminobenzoate (0.080 g) and 4-dimethylaminopyridine (one pellet), and the mixture was stirred overnight. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: ethyl acetate:n-hexane=1:5) to obtain methyl 2-methoxy-4-[(5,6,7,7a,8,9,10,11-octahydro-4H-2-benzo[ef]heptalenyl)carboxamido]benzoate (0.072 g, yield: 48%).

$^1$H-NMR (400 MHz, CDCl$_3$): δ 1.51-1.70 (6H, m), 1.79-1.97 (6H, m), 2.94 (4H, t, J=5.7 Hz), 3.25-3.32 (1H, m), 3.88 (3H, s), 3.95 (3H, s), 6.96 (1H, dd, J=8.7, 2.1 Hz), 7.42 (2H, s), 7.82 (1H, d, J=2.1 Hz), 7.85 (1H, d, J=8.7 Hz), 7.96 (1H, br-s)

A suspension of the aforementioned ester in ethanol (5 ml) was added with 2 N aqueous sodium hydroxide (1 ml), and the mixture was stirred at room temperature for 3 hours. The reaction mixture was made acidic with 2 N aqueous hydrochloric acid, and the mixture was extracted with chloroform. The organic layer was washed with saturated brine, dried over anhydrous sodium sulfate, and then concentrated under reduced pressure, and the resulting residue was recrystallized from ethyl acetate-n-hexane to obtain the title compound (0.054 g, yield: 86%) as colorless needles (melting point: 233-234° C.).

$^1$H-NMR (400 MHz, DMSO-d$_6$): δ 1.43-1.56 (6H, m), 1.72-1.91 (6H, m), 2.88 (4H, t, J=5.4 Hz), 3.06-3.15 (1H, m), 3.78 (3H, s), 7.43 (1H, d, J=8.7 Hz), 7.50 (2H, s), 7.56-7.63 (2H, m), 10.21 (1H, s)

Example 33

6-[(5,6,7,7a,8,9,10,11-Octahydro-4H-2-benzo[ef]heptalenyl)carbamoyl]nicotinic acid

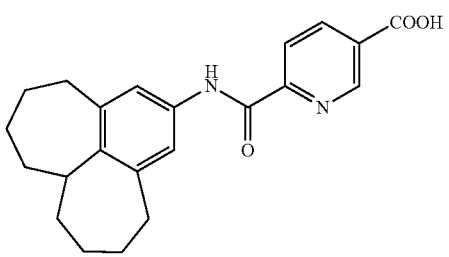

[Formula 80]

A suspension of pyridine-2,5-dicarboxylic acid 5-methyl ester (0.062 g) in anhydrous benzene (3 ml) was added with thionyl chloride (1 ml), and the mixture was refluxed by heating for 3 hours. The reaction mixture was concentrated under reduced pressure, the resulting residue was dissolved in anhydrous benzene (2 ml) and pyridine (1 ml), the solution was added with a solution of 5,6,7,7a,8,9,10,11-octahydro-4H-2-benzo[ef]heptalenylamine (0.070 g) in anhydrous benzene (1 ml), and the mixture was stirred at room temperature for 4 hours. The reaction mixture was added with 2 N aqueous hydrochloric acid and thereby made acidic, and the mixture was extracted with ethyl acetate. The organic layer was washed successively with water, 10% aqueous sodium carbonate, water and saturated brine, and then dried over anhydrous sodium sulfate. The organic layer was concentrated under reduced pressure, and the resulting residue was purified by silica gel column chromatography (developing solvent: ethyl acetate:n-hexane=1:20), and then recrystallized from chloroform-n-hexane to obtain methyl 6-[(5,6,7,7a,8,9,10,11-octahydro-4H-2-benzo[ef]heptalenyl)carbamoyl]nicotinate (0.094 g, yield: 87%) as pale yellow needles (melting point: 139-140° C.).

$^1$H-NMR (400 MHz, CDCl$_3$): δ 1.51-1.69 (6H, m), 1.79-1.94 (6H, m), 2.87 (4H, t, J=5.4 Hz), 3.19-3.26 (1H, m), 4.00 (3H, s), 7.38 (2H, s), 8.36 (1H, d, J=8.1 Hz), 8.49 (1H, dd, J=8.1, 1.8 Hz), 9.18 (1H, d, J=1.8 Hz), 9.86 (1H, br-s)

A suspension of the aforementioned ester (0.090 g) in ethanol (5 ml) was added with 2 N aqueous sodium hydroxide (1 ml), and the mixture was stirred at room temperature for 6 hours. The reaction mixture was made acidic with 2 N aqueous hydrochloric acid, and the mixture was extracted with chloroform. The organic layer was washed with saturated brine, dried over anhydrous sodium sulfate, and then concentrated under reduced pressure, and the resulting residue was recrystallized from ethyl acetate-n-hexane to obtain the title compound (0.081 g, yield: 93%) as pale yellow needles (melting point: 239-240° C.).

$^1$H-NMR (400 MHz, DMSO-d$_6$): δ 1.53-1.66 (6H, m), 1.79-1.91 (6H, m), 2.84-2.88 (4H, m), 3.19-3.26 (1H, m), 7.38 (2H, s), 8.39 (1H, d, J=8.1 Hz), 8.54 (1H, d, J=8.1), 9.24 (1H, s), 9.86 (1H, s)

Example 34

6-[(5,6,7,7a,8,9,10,11-Octahydro-4H-2-benzo[ef]heptalenyl)carboxamido]nicotinic acid

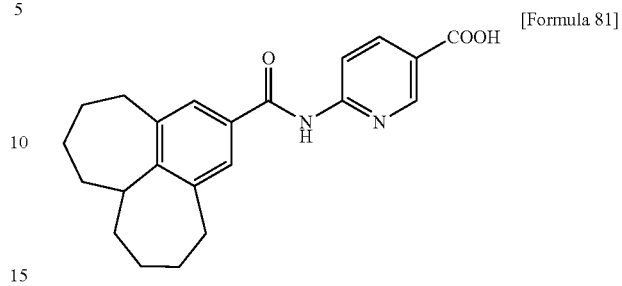

[Formula 81]

A suspension of 5,6,7,7a,8,9,10,11-octahydro-4H-2-benzo[ef]heptalenecarboxylic acid (0.072 g) in anhydrous benzene (3 ml) was added with thionyl chloride (2 ml), and the mixture was refluxed by heating for 3 hours. The reaction mixture was concentrated under reduced pressure, the resulting residue was dissolved in anhydrous benzene (2 ml) and pyridine (2 ml), the solution was added with methyl 6-aminonicotinate (0.050 g) and 4-dimethylaminopyridine (one pellet), and the mixture was stirred overnight. The reaction mixture was added with 2 N aqueous hydrochloric acid and thereby made acidic, and the mixture was extracted with ethyl acetate. The organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: ethyl acetate:n-hexane=1:20) to obtain methyl 6-[(5,6,7,7a,8,9,10,11-octahydro-4H-2-benzo[ef]heptalenyl)carboxamido]nicotinate (0.009 g, yield: 8%).

$^1$H-NMR (400 MHz, CDCl$_3$): δ 1.50-1.71 (6H, m), 1.79-1.99 (6H, m), 2.92 (4H, t, J=5.4 Hz), 3.26-3.33 (1H, m), 3.94 (3H, s), 7.49 (2H, s), 8.34 (1H, dd, J=9.0, 2.1 Hz), 8.47 (1H, d, J=9.0 Hz), 8.74 (1H, br-s), 8.93 (1H, d, J=2.1 Hz)

A suspension of the aforementioned ester (0.016 g) in ethanol (3 ml) was added with 2 N aqueous sodium hydroxide (1 ml), and the mixture was stirred at room temperature for 3 hours. The reaction mixture was made acidic with 2 N aqueous hydrochloric acid, and the mixture was extracted with chloroform. The organic layer was washed with saturated brine, dried over anhydrous sodium sulfate, and then concentrated under reduced pressure, and the resulting residue was recrystallized from ethanol-chloroform to obtain the title compound (0.012 g, yield: 80%) as colorless needles (melting point: >300° C.).

$^1$H-NMR (400 MHz, DMSO-d$_6$): δ 1.44-1.62 (6H, m), 1.73-1.93 (6H, m), 2.87-2.91 (4H, m), 3.25-3.68 (1H, m), 7.63 (2H, s), 8.28-8.91 (2H, m), 8.86 (1H, s), 10.87 (2H, s)

Example 35

2,6-Difluoro-4-[(5,6,7,7a,8,9,10,11-octahydro-4H-2-benzo[ef]heptalenyl)carboxamido]benzoic acid

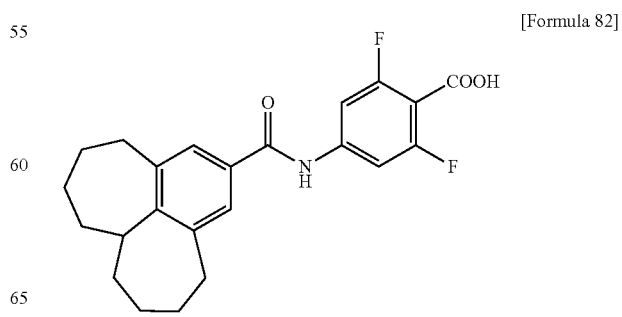

[Formula 82]

5,6,7,7a,8,9,10,11-Octahydro-4H-2-benzo[ef]heptalen-ecarboxylic acid (0.053 g) and cyanuric chloride (0.060 g) were suspended in acetone (3 ml), the suspension was added with triethylamine (0.091 ml), and the mixture was stirred at room temperature for 3 hours. The reaction mixture was added with ethyl 2,6-difluoro-4-amino-benzoate (0.079 g), the mixture was stirred for 3 hours, then the solvent was evaporated, the residue was added with pyridine (5 ml) and 4-dimethylaminopyridine (one pellet), and the mixture was stirred overnight at 60° C. The reaction mixture was left to cool and then added with 2 N aqueous hydrochloric acid and thereby made acidic, the mixture was extracted with ethyl acetate, and the organic layer was washed successively with water, 10% aqueous sodium carbonate, and saturated brine, and dried over anhydrous sodium sulfate. The organic layer was concentrated under reduced pressure, and the resulting residue was purified by silica gel column chromatography (developing solvent: ethyl acetate:n-hexane=1:20) to obtain ethyl 2,6-difluoro-4-[(5,6,7,7a,8,9,10,11-octahydro-4H-2-benzo[ef]heptalenyl)carboxamido]benzoate (0.042 g, yield: 45%).

$^1$H-NMR (400 MHz, CDCl$_3$): δ 1.39 (3H, t, J=7.2 Hz), 1.50-1.70 (6H, m), 1.79-1.97 (6H, m), 2.90 (4H, t, J=5.7 Hz), 3.22-3.32 (1H, m), 4.40 (2H, q, J=7.2 Hz), 7.36 (2H, d, J=9.9 Hz), 7.39 (2H, s), 7.98 (1H, br-s)

A suspension of the aforementioned ester (0.042 g) in ethanol (5 ml) was added with 2 N aqueous sodium hydroxide (1 ml), and the mixture was stirred at 60° C. for 2 hours. The reaction mixture was made acidic with 2 N aqueous hydrochloric acid, and the mixture was extracted with chloroform. The organic layer was washed with saturated brine, dried over anhydrous sodium sulfate, and then concentrated under reduced pressure, and the resulting residue was recrystallized from ethyl acetate-n-hexane to obtain the title compound (0.030 g, yield: 77%) as colorless needles (melting point: 263-264° C.).

$^1$H-NMR (400 MHz, DMSO-d$_6$): δ 1.45-1.62 (6H, m), 1.73-1.94 (6H, m), 2.90 (4H, t, J=6.0 Hz), 3.26-3.34 (1H, m), 7.51 (2H, s), 7.61 (2H, d, J=10.8 Hz), 10.56 (1H, s)

Test Example 1

Cells of human acute promyelocytic leukemia cell strain HL-60 were cultured in a CO$_2$ incubator (5% CO$_2$, 37° C.) using the RPMI medium containing 5% FBS. Differentiation inducing actions of the compounds of the present invention prepared in the above examples (all were carboxylic acid compounds) on the HL-60 cells were evaluated on the basis of ability to reduce nitroblue tetrazolium (NBT) determined by observing differentiation from promyelocytic cells into granulocytic cells as an index. The cells that entered into the logarithmic phase and reached a substantially confluent state were centrifuged at 1000 rpm for 5 minutes, and the culture supernatant was removed. The cell pellet was suspended in fresh RPMI medium containing 5% FBS at a density of 8.0× 10$^4$ cells/ml, then the suspension was added with a test compound dissolved in DMSO at an intended concentration, and the cells were cultured for four days and then used for the experiment. The samples were prepared so as to have the same DMSO concentration.

Cell count of the cells after the culture for a predetermined period was determined by a cell counting method using a blood cell counting chamber. The NBT-reducing ability was obtained as follows. NBT was dissolved in phosphate buffered saline (PBS(-)) at a concentration of 0.2%, and the solution was added with an equivalent volume of the RPMI medium containing 5% FBS. The mixture was added with phorbol 12-myristate 13-acetate (tPA) at a concentration of 0.2 μM (about 200 ng) to prepare a reagent solution. The collected cells were centrifuged at 1000 rpm for 5 minutes, the supernatant was removed, and the remained cell pellet was added with the reagent solution. The mixture was incubated on a water bath at 37° C. for 20 minutes, and then NBT-reduced stained positive cells were counted by using the counting chamber to calculate a differentiation induction ratio. The results are shown in Table 1. All the compounds of the present invention had potent differentiation-inducing action on the HL-60 cells.

TABLE 1

| Compound | Differentiation induction ratio (%) | | | |
|---|---|---|---|---|
| | 1 × 10$^{-9}$ M | 1 × 10$^{-8}$ M | 1 × 10$^{-7}$ M | 1 × 10$^{-6}$ M |
| Example 1 | 5.0 | 6.6 | 18.3 | — |
| Example 2 | 9.5 | 26.7 | 37.5 | — |
| Example 3 | — | 48.5 | 60.1 | 65.6 |
| Example 4 | — | 16.3 | 36.7 | 47.8 |
| Example 5 | — | 23.6 | 41.8 | 50.4 |
| Example 7 | — | 2.1 | 4.5 | 40.2 |
| Example 8 | — | 53.5 | 59.2 | 68.9 |
| Example 15 | 14.9 | 30.9 | — | — |
| Example 16 | — | 18.4 | 29.2 | 33.8 |
| Example 17 | — | 19 | 21.4 | 24.4 |
| Example 18 | — | 16.6 | 32.1 | 30.6 |
| Example 20 | — | 5.3 | 15.9 | 26.4 |
| Example 21 | — | 41.4 | 60.5 | 62.1 |
| Example 27 | 4.6 | 12.8 | 52.8 | — |
| Example 28 | 22.7 | 55.5 | 52.7 | — |

INDUSTRIAL APPLICABILITY

The compound of the present invention, a salt thereof, and an ester thereof have a retinoid action, and can be used as a medicament for prophylactic and/or therapeutic treatment for various kinds of diseases which can be prevented and/or cured with a retinoid such as retinoic acid.

What is claimed is:

1. A compound represented by the following general formula (I):

[Formula 1]

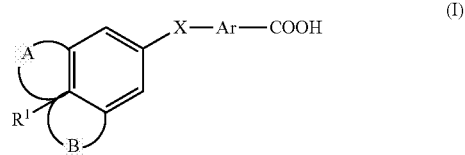

wherein
R$^1$ represents a hydrogen atom or a C$_{1-6}$ alkyl group;
A and B independently represent —(CH$_2$)$_2$—, —(CH$_2$)$_3$— or —(CH$_2$)$_4$—;
X represents
—N(R$^2$)—CO—, wherein R$^2$ represents a hydrogen atom or a C$_{1-6}$ alkyl group,
—CO—N(R$^3$)—, wherein R$^3$ represents a hydrogen atom or a C$_{1-6}$ alkyl group, —C($R^4$)=C($R^5$)—, wherein $R^4$ and $R^5$ independently represent a hydrogen atom or a $C_{1-6}$ alkyl group, or —N($R^6$)—$SO_2$—, wherein $R^6$ represents a hydrogen atom or a $C_{1-6}$ alkyl group; and Ar represents an aryldiyl group or a heteroaryldiyl group, wherein the aryldiyl group and the heteroaryldiyl group may have a substituent, a salt thereof, or an ester thereof.

2. The compound, a salt thereof, or an ester thereof according to claim 1, wherein $R^1$ is a hydrogen atom or a methyl group, A and B both represent —$(CH_2)_3$— or both represent —$(CH_2)_4$—, X is —NH—CO— or —CO—NH—, and Ar is a phenylene group, a monofluorophenylene group, a monochlorophenylene group, a monohydroxyphenylene group, a monoalkoxyphenylene group, a pyridinediyl group, or a thiophenediyl group.

3. A pharmaceutical composition comprising the compound according to claim 1 or a physiologically acceptable salt thereof as an active ingredient and a pharmaceutically acceptable additive.

4. A compound represented by the general formula (I):

[Formula 1]

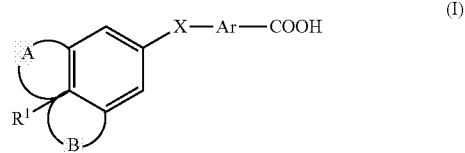

wherein $R^1$ represents a hydrogen atom or a $C_{1-6}$ alkyl group;

A and B independently represent —$(CH_2)_2$—, —$(CH_2)_3$— or —$(CH_2)_4$—; and

X—Ar—COOH is X', and X' is —COOH or —$NH_2$, or a salt thereof.

5. A pharmaceutical composition comprising the compound according to claim 2 or a physiologically acceptable salt thereof as an active ingredient and a pharmaceutically acceptable additive.

* * * * *